US012239833B2

(12) United States Patent
Van Welie et al.

(10) Patent No.: US 12,239,833 B2
(45) Date of Patent: Mar. 4, 2025

(54) ADAPTIVE CLOSED-LOOP DBS STIMULATION CONTROL

(71) Applicant: Neural Dynamics Technologies Inc., Boston, MA (US)

(72) Inventors: Ingrid Van Welie, Newton, MA (US); Girish Rughoobur, Cambridge, MA (US)

(73) Assignee: Neural Dynamics Technologies Inc., MA (US)

( * ) Notice: Subject to any disclaimer, the term of this patent is extended or adjusted under 35 U.S.C. 154(b) by 0 days.

(21) Appl. No.: 18/594,082

(22) Filed: Mar. 4, 2024

(65) Prior Publication Data

US 2024/0285937 A1 Aug. 29, 2024

Related U.S. Application Data

(63) Continuation of application No. PCT/US2024/017059, filed on Feb. 23, 2024.
(Continued)

(51) Int. Cl.
*A61N 1/05* (2006.01)
*A61B 5/00* (2006.01)
(Continued)

(52) U.S. Cl.
CPC .......... *A61N 1/0534* (2013.01); *A61B 5/0031* (2013.01); *A61B 5/293* (2021.01); *A61B 5/304* (2021.01); *A61B 5/31* (2021.01); *A61B 5/7225* (2013.01); *A61N 1/36132* (2013.01); *A61N 1/36139* (2013.01); *A61N 1/36146* (2013.01);
(Continued)

(58) Field of Classification Search
CPC .......................... A61N 1/0534; A61N 1/36146
See application file for complete search history.

(56) References Cited

U.S. PATENT DOCUMENTS 8,010,208 B2  8/2011  Nimer et al.
8,321,025 B2  11/2012  Bedenbaugh et al.
(Continued)

FOREIGN PATENT DOCUMENTS

WO  2017062577 A2  4/2017
WO  2020049512 A1  3/2020
WO  2020152628 A2  7/2020

*Primary Examiner* — Alyssa M Alter
(74) *Attorney, Agent, or Firm* — Finnegan, Henderson, Farabow, Garrett & Dunner LLP

(57) ABSTRACT

Systems and methods are disclosed for deep brain stimulation. In one implementation, a deep brain stimulation system comprises a neural probe configured for placement within a brain; at least one signal lead; a sensing assembly including at least one sensing micro-electrode and at least one stimulation electrode; and at least one processor assembly configured to: receive at least one sense signal generated in response to interaction between the at least one sensing electrode and one or more electrical signals generated by at least one neuron in the brain; deliver at least one of a library of preset target stimulation patterns; determine a target stimulation pattern based on at least one characteristic of the at least one sense signal; and cause a signal generator to deliver stimulation signals to stimulation electrodes among the at least one stimulating electrode to activate the set of stimulation electrodes according to the target stimulation pattern.

19 Claims, 17 Drawing Sheets

Related U.S. Application Data

(60) Provisional application No. 63/447,996, filed on Feb. 24, 2023.

(51) Int. Cl.
    *A61B 5/293*     (2021.01)
    *A61B 5/304*     (2021.01)
    *A61B 5/31*     (2021.01)
    *A61N 1/36*     (2006.01)
    *A61N 1/378*     (2006.01)

(52) U.S. Cl.
    CPC .... *A61N 1/3787* (2013.01); *A61B 2560/0219* (2013.01); *A61B 2562/125* (2013.01)

(56) References Cited

U.S. PATENT DOCUMENTS

| | | |
|---|---|---|
| 8,929,992 B2 | 1/2015 | Toader et al. |
| 9,119,543 B2 | 9/2015 | Martens et al. |
| 2014/0288602 A1 | 9/2014 | McCormack et al. |
| 2021/0031043 A1* | 2/2021 | Esteller .............. A61N 1/36082 |

* cited by examiner

ADAPTIVE CLOSED-LOOP DBS STIMULATION CONTROL

CROSS-REFERENCE TO RELATED APPLICATIONS

The application is a continuation of PCT International Application No. PCT/US2024/17059, filed Feb. 23, 2024, which is based upon and claims priority to U.S. Provisional Application No. 63/447,996, filed Feb. 23, 2023, the entire contents of all of which are incorporated herein by reference. This invention was made with government support under grant identifier number R44MH118155 awarded by the National Institute of Mental Health (NIMH) of the National Institutes of Health (NIH). The government has certain rights in the invention.

TECHNICAL FIELD

The present disclosure relates generally to neural interface systems and methods thereof, and in particular, to systems and methods for creating a closed loop, implantable neural interface consisting of arrays of micro-electrodes.

BACKGROUND

For most neurological disorders, few adequate treatment options exist. One reason for this is a lack of understanding of how the brain controls and mediates behavior and how it malfunctions in disease states. One challenge for modern neuroscience is therefore to understand how neuronal activity mediates behavior at a single neuron level and across multiple timescales. Since the early twentieth century, neural activity has been studied using electrodes. Electrodes can be inserted into the brain to arbitrary depths to record from both the brain surface and deeper brain regions. The latest innovation in this field has come from the development of ultra-high density neural recording probes, i.e., recording electrodes micro-fabricated on silicon substrates with channel counts upwards of 256. High-channel count electrodes do not only allow sampling from higher numbers of neurons simultaneously, but sampling from large numbers of recording sites within close proximity of each other, also helps spike-sorting algorithms more accurately sort neurons based on spike amplitude and waveform.

Such high-density electrode designs alone, however, do not address the issue that the brain consists of many non-homogenous brain structures, each with its own distinct morphology and anatomical arrangement. Each brain region consists of layers and groups of neurons that are organized in unique ways, and each neuron type has its own distinct morphology. In view of these differences, electrodes designed to operate in one region of the brain may be ineffective in other regions of the brain. Further, existing designs lack the ability to individually control electrodes in an electrode pattern to accomplish appropriate sensing and stimulation unique to the geometry of distinct brain regions. Thus, there is a need for neural interfaces that offer an increased level of customizability for deployment in different regions of the brain.

Micro-electrodes in general are mostly used in research studies however, and predominantly in animal models. In a clinical setting, micro-electrodes are used to find and identify small, deep brain regions by recording action potential firing patterns of single neurons for subsequent implantation of stimulation electrodes, as for example done during surgery for the implantation of deep brain stimulation electrodes for the treatment of Parkinson's. After stimulation electrodes are placed however, it is not possible to record local single neuron responses any longer. Closed-loop micro-electrodes that could record and stimulate would enable continuous sensing of local neural activity down to the single neuron level and would allow for responsive local stimulation. Thus, there is a need for the development of micro-electrodes that can both sense and stimulate down to the single neuron level. The presently disclosed systems are aimed at addressing this need and may include neural interface systems offering different electrode layouts targeting different brain regions and individual electrode control allowing switching between sensing and/or stimulation functionalities such that the disclosed systems may be flexibly deployed across a wide range of brain regions in the context of deep brain stimulation.

SUMMARY

Systems and methods for creating a closed loop, implantable neural interface consisting of arrays of micro-electrodes are disclosed. A neural interface may comprise a neural probe configured for placement within a brain; at least one signal lead extending from the neural probe towards an external processing unit; and a sensing assembly included on the neural probe. The sensing assembly may include a plurality of dual-role micro-electrodes positioned on the neural probe, wherein each of the dual-role electrodes is configured to sense electrical signals generated by one or more neurons in the brain and to convey to the at least one signal lead one or more sense signals generated based on the sensed electrical signals, and wherein each of the dual-role micro-electrodes is configured to receive, via the at least one signal lead, a stimulation signal selectively delivered from a stimulus generator located within an external processing unit.

In some embodiments, the at least one signal lead includes a plurality of conductors, such that each of the plurality of dual-role electrodes is associated with a single conductor configured to both carry sensed signals from and to deliver a stimulation signal to one of the plurality of dual-role electrodes. In some embodiments, the at least one signal lead includes a plurality of conductors, such that each of the plurality of dual-role electrodes is associated with at least two conductors, wherein a first of the at least two conductors is configured to carry sensed signals from a particular one of the plurality of dual-role electrodes, and a second of the at least two conductors, different from the first of the at least two conductors, is configured to deliver a stimulation signal to the particular one of the plurality of dual-role electrodes.

In some embodiments, stimulation signals selectively delivered from the signal generator to corresponding ones of the plurality of electrodes cause activation of at least some of the plurality of electrodes according to a selected stimulation pattern. In some embodiments, stimulation signals selectively delivered from the signal generator to corresponding ones of the plurality of electrodes cause activation during a first time period of a first set of the plurality of electrodes to provide a first stimulation pattern and cause activation, during a second time period different from the first time period of a second set of the plurality of electrodes to provide a second stimulation pattern.

In some embodiments, each of the plurality of electrodes comprises at least one conductor. In some embodiments, the at least one conductor includes a surface comprising a surface area between 25 and 400 square microns. In some embodiments, the at least one conductor comprises gold, titanium nitride or platinum iridium, iridium oxide or some other well conducting and biocompatible metal. In some embodiments, each of the plurality of electrodes has an impedance of between 1 kOhms and 1 MOhm.

In some embodiments, the sensing assembly comprises circuitry operable to switch each of the plurality of electrodes between a sensing mode and a stimulation mode. In some embodiments, the plurality of electrodes is arranged in at least one array. In some embodiments, the neural probe comprises at least one facet on which at least some of the plurality of electrodes are disposed. In some embodiments, the neural probe comprises two facets, including a first facet and a second facet on opposing faces of the neural probe, on which at least some of the plurality of electrodes are disposed. In some embodiments, the neural probe comprises three facets on which at least some of the plurality of electrodes are disposed. In some embodiments, the neural probe comprises four facets on which at least some of the plurality of electrodes are disposed.

In some embodiments, the neural probe is non-centric. In some embodiments, the one or more sense signals are amplified by an amplifier local to the neural probe. In some embodiments, in response to a delivered stimulation signal, each of the plurality of electrodes is configured to cause emission of an electrical field extending into the brain by at least 100 microns. In some embodiments, each of the plurality of electrodes is configured to sense electrical signals generated by brain neurons located within a range of up to 200 microns. In some embodiments, the neurostimulator further comprises a power assembly configured to be located on the skull of the brain that can be charged via electrodynamic wireless power transmission, inductive power transmission, or resonant power coupling.

Systems and methods for providing a system for local amplification and multiplexing and analog-to-digital conversion of signals sensed from deep brain regions are disclosed. A system for local amplification and multiplexing and analog-to-digital conversion of signals sensed from deep brain regions may comprise a neural probe with a sensing assembly configured for placement within a brain and at least one signal lead extending from the neural probe towards an external processing unit. The sensing assembly may include a plurality of electrodes positioned on the neural probe, wherein one or more of the plurality of electrodes are configured to sense electrical signals generated by one or more neurons in the brain; at least one amplifier configured to generate at least one amplification signal based on the sensed electrical signals generated by the one or more neurons and at least one multiplexer configured to multiplex at least two amplified signals based on the sensed electrical signals generated by the one or more neurons, wherein the at least one multiplexed signal is carried by the at least one signal lead toward a location outside of the brain. The processing unit located outside of the brain will contain at least one analog-to-digital converter configured to convert at least one amplified signal based on the sensed electrical signals generated by the one or more neurons to at least one digital signal; a power unit for both powering the neural probe and for delivering electrical stimuli, and a chip for processing incoming digital signals and for controlling pulse generation.

In some embodiments, the at least one signal lead includes one or more electrical conductors. In some embodiments, the at least one signal lead has a length of at least 60 millimeters. In some embodiments, the at least one signal lead has a length of at least 80 millimeters. In some embodiments, the at least one signal lead has a length of at least 100 millimeters. In some embodiments, the at least one amplifier includes at least one of a low-noise operational transconductance amplifier, a Miller operational transconductance amplifier, a current mirror operational transconductance amplifier, or a differential self-biased operational transconductance amplifier.

In some embodiments, the one or more of the plurality of electrodes are configured to sense electrical signals from neurons within a 100-micron radius from an area of the neural probe on which the one or more of the plurality of electrodes are located. In some embodiments, the at least one amplifier is configured to vary a gain associated with the at least one amplification signal based on at least one characteristic of the sensed electrical signals. In some embodiments, the at least one amplifier is configured to generate the at least one amplification signal for the at least one electrode based on a magnitude of a signal received at the at least one electrode. In some embodiments, the at least one amplifier is configured to generate the at least one amplification signal for the at least one electrode based on a position of the at least one electrode on the neural probe.

In some embodiments, the sensing assembly further comprises at least one filter configured to condition the sensed electrical signals or the at least one amplification signal. In some embodiments, the sensing assembly is configured to multiplex a plurality of amplified signals to reduce the number of conductors exiting the sensing assembly. In some embodiments, the sensing assembly is configured to convert a plurality of analog signals into digital signals to enable read-out of the data on a computer interface. In some embodiments, the system for local amplification, multiplexing and analog-to-digital conversion of signals sensed from deep brain regions further comprises a power assembly configured to be located on a skull of the brain and to provide power to the sensing assembly located inside the brain. In some embodiments, the power assembly is configured to be charged via electrodynamic wireless power transmission, inductive power transmission, or resonant power coupling.

Additional objects and advantages of the embodiments will be set forth in part in the description that follows, and in part will be obvious from the description or may be learned by practice of the embodiments. The objects and advantages of the embodiments will be realized and attained by means of the elements and combinations particularly pointed out in the appended claims.

It is to be understood that both the foregoing general description and the following detailed description are exemplary and explanatory only and are not restrictive of the claims.

BRIEF DESCRIPTION OF DRAWING(S)

The accompanying drawings, which are incorporated in and constitute a part of this specification, illustrate disclosed embodiments and, together with the description, serve to explain the disclosed embodiments. The particulars shown are by way of example and for purposes of illustrative discussion of embodiments of the present disclosure. The drawings and components shown therein may not be to scale. The description taken with the drawings makes apparent to those skilled in the art how embodiments of the present disclosure may be practiced.

Figure 13A:
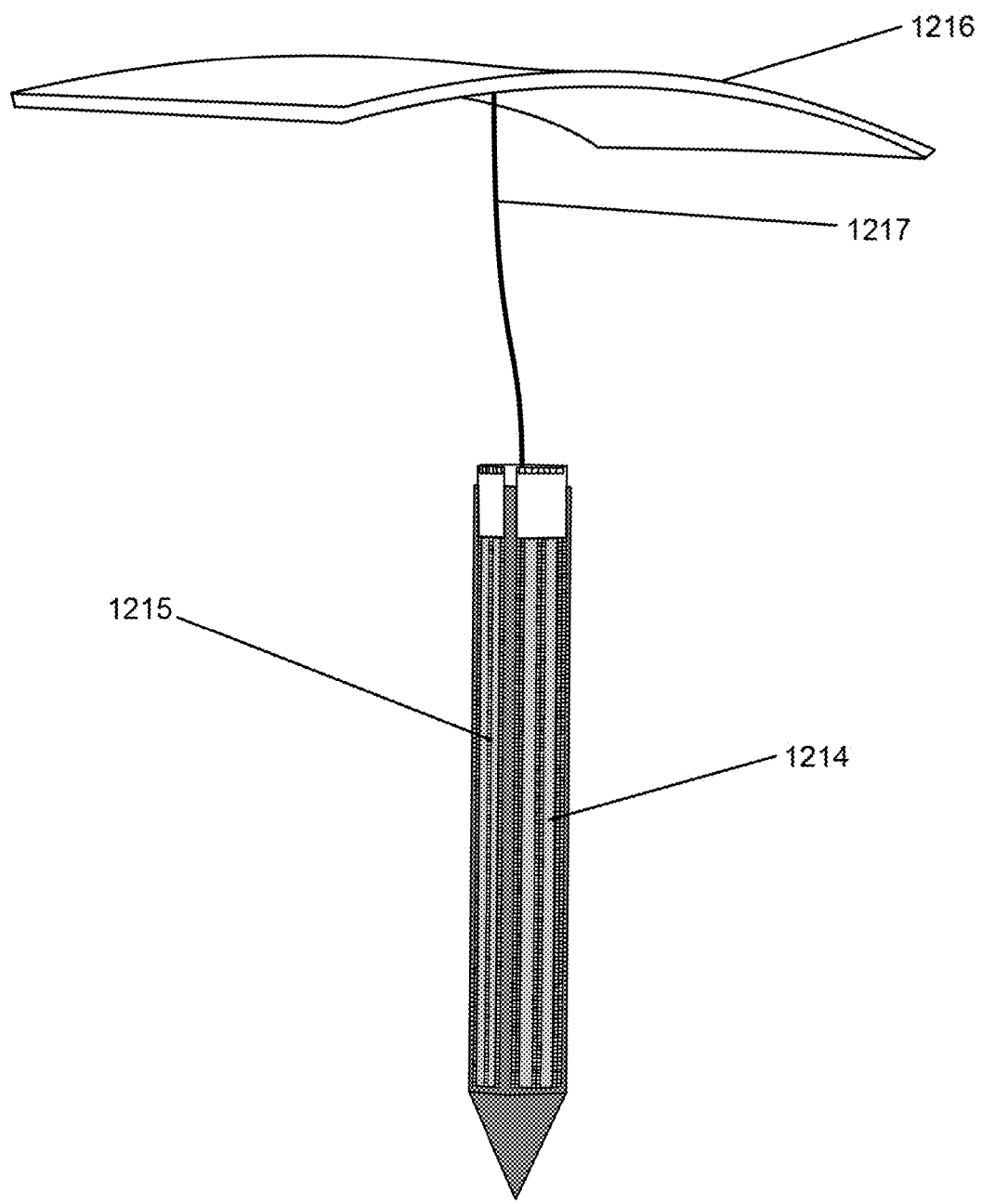

FIG. 13A diagrammatically illustrates a perspective view of components of a deep brain stimulation system in accordance with embodiments of the present disclosure.

Figure 13B:
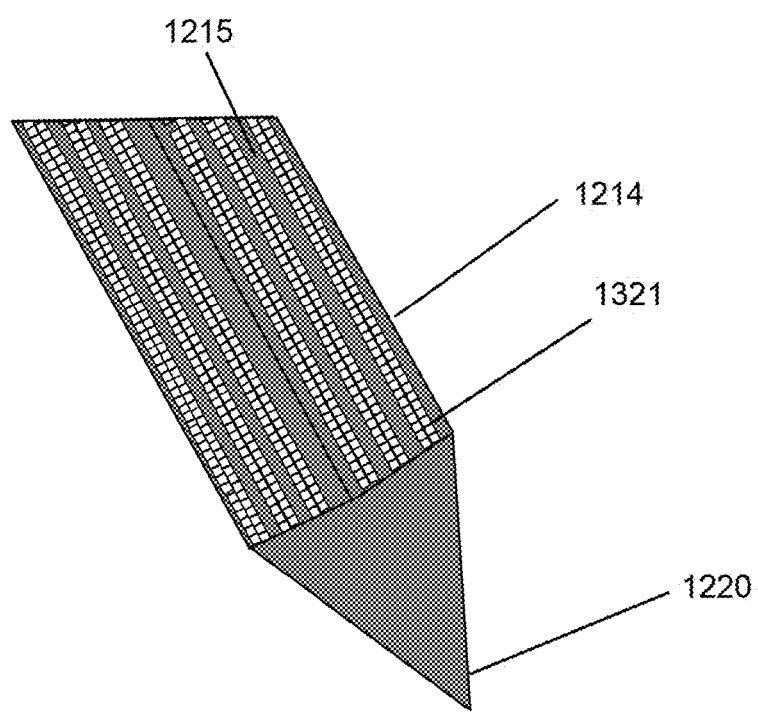

FIG. 13B diagrammatically illustrates a perspective view of a neural probe of a deep brain stimulation system according to embodiments of the present disclosure.

Figure 14:
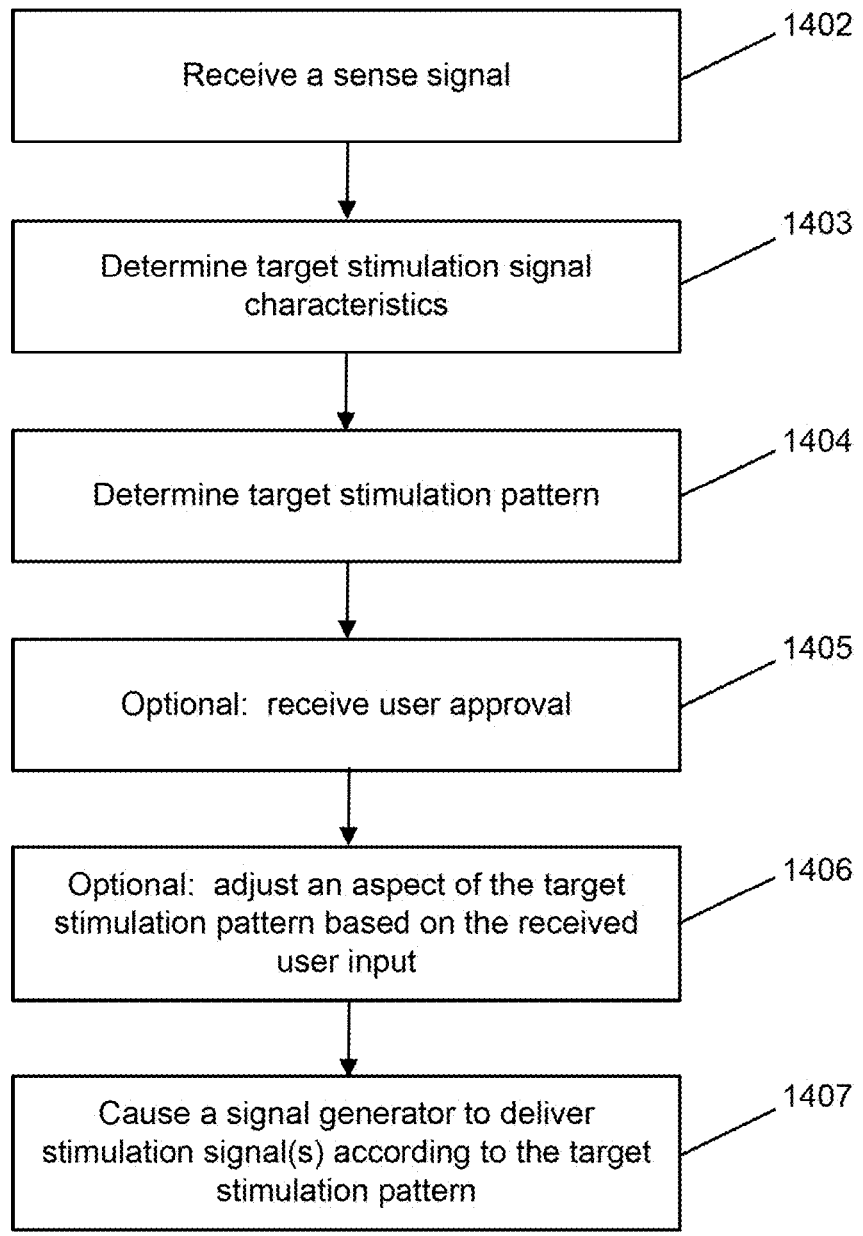

FIG. 14 provides a flow diagram of an exemplary method performed by embodiments of the present disclosure.

DETAILED DESCRIPTION

Individually Controlled, Dual-Role Micro-Electrodes

Recognizing the need for improved targeting precision, closed-loop sensing, improved battery life and patient comfort as relevant to implantable neural electrodes, particularly electrodes used in deep brain stimulation, systems and methods for deep brain stimulation and sensing using arrays of micro electrodes are disclosed.

Figure 1:
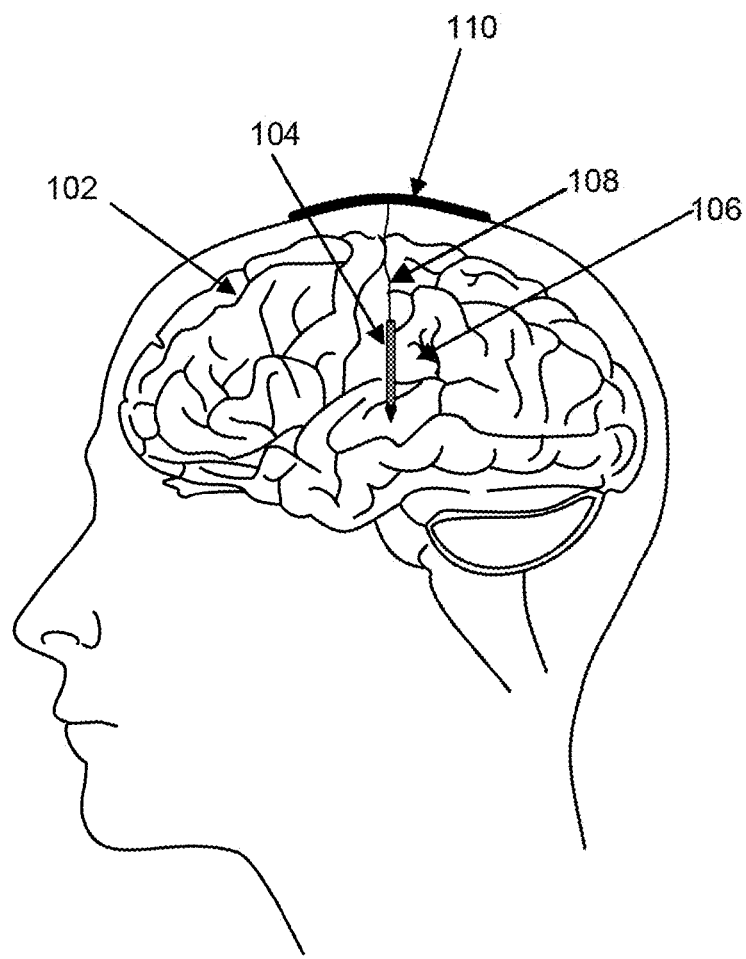
FIG. 1 illustrates the components of a deep-brain sensing system, consistent with some embodiments of the present disclosure.

FIG. 1 illustrates the components of a deep-brain sensing and stimulation system, consistent with some embodiments of the present disclosure. As shown in FIG. 1, a system for deep-brain sensing and stimulation is inserted into a deep brain region 106 of the brain 102. Deep brain 106 may include regions such as the subthalamic nucleus, globus pallidus, the thalamus, or any other subcortical brain region. Sensing signals from deep brain regions may be desirable for helping clinicians directly identify deep brain structures relevant to present and future medical applications, such as diagnosis and treatment of diseases associated with deep brain regions. In one example, deep brain region 106 may include the thalamus since the thalamus is associated with epilepsy. In another example, deep brain region 106 may include the basal ganglia and/or the globus pallidus since these regions are associated with Parkinson's disease. As shown in FIG. 1, a system for deep brain sensing and stimulation includes a neural probe with arrays of micro-electrodes 104, which is inserted into the brain 102 in a deep brain region 106 and connected via a signal lead 108 to an external processing unit 110.

Figure 2:
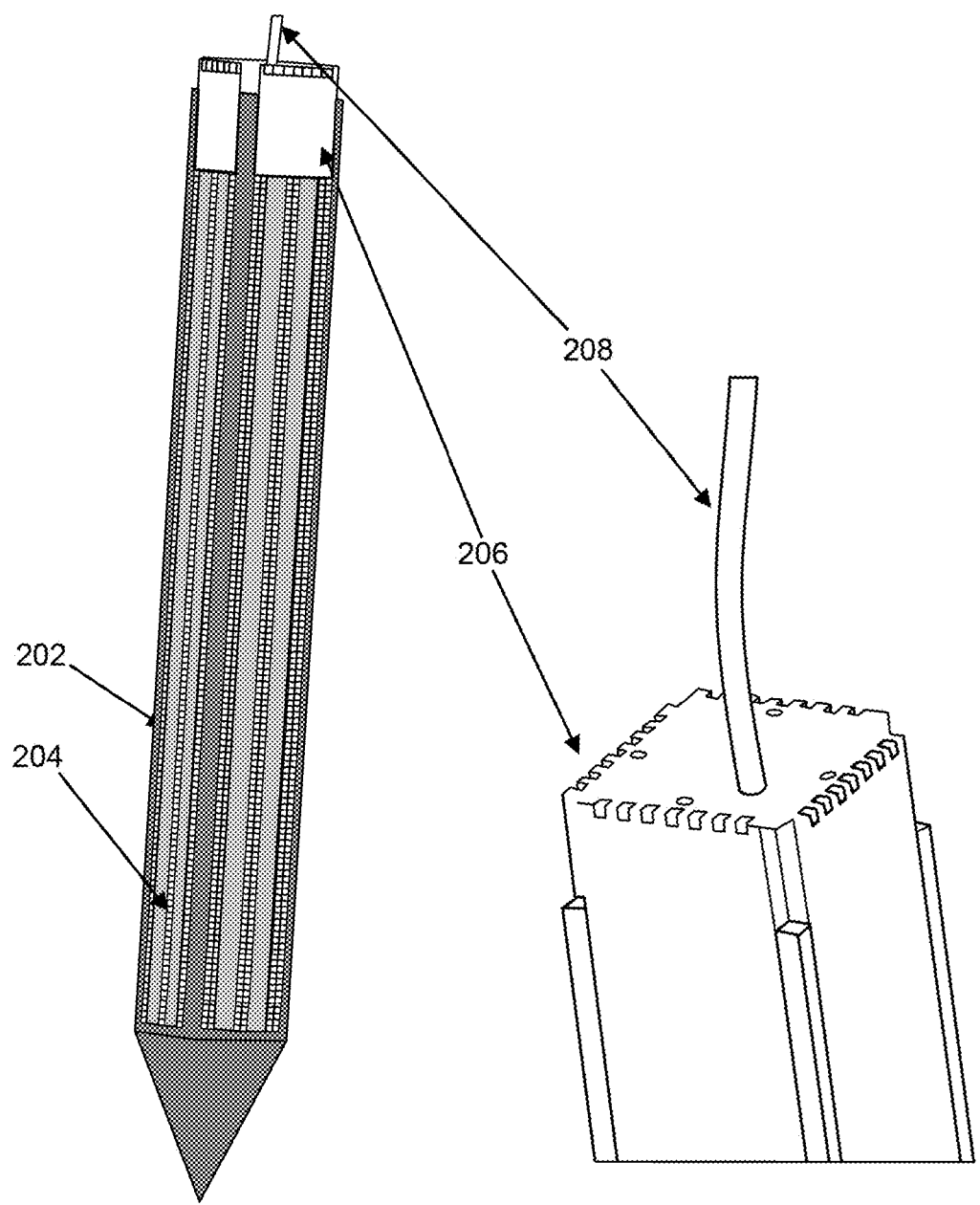
FIG. 2 illustrates one exemplary configuration of a neural probe, consistent with some embodiments of the present disclosure.

FIG. 2 illustrates one exemplary configuration of a neural probe, consistent with some embodiments of the present disclosure. As shown in FIG. 2, the neural probe may include a shaft 202, which is inserted into the brain, such as in a deep brain region. The shaft may include a micro-electrode assembly 204, which may include a plurality of electrodes for sensing, stimulating, or a combination of the two. The micro electrode assembly 204 may be positioned anywhere on the shaft 202. The micro electrode assembly can also be arranged differently for different brain regions. The sensing probe may also include circuitry 206 for amplification and multiplexing of data and switching circuitry. An external processing unit is connected to the implanted neural probe via the signal lead 208. The processing unit may act as an interface for external connections such as leads, wires, circuits, or any other electrical components. The processing unit also houses the stimulus generator and may have components allowing for wireless power charging and for wireless data transfer and communications.

Figure 3:
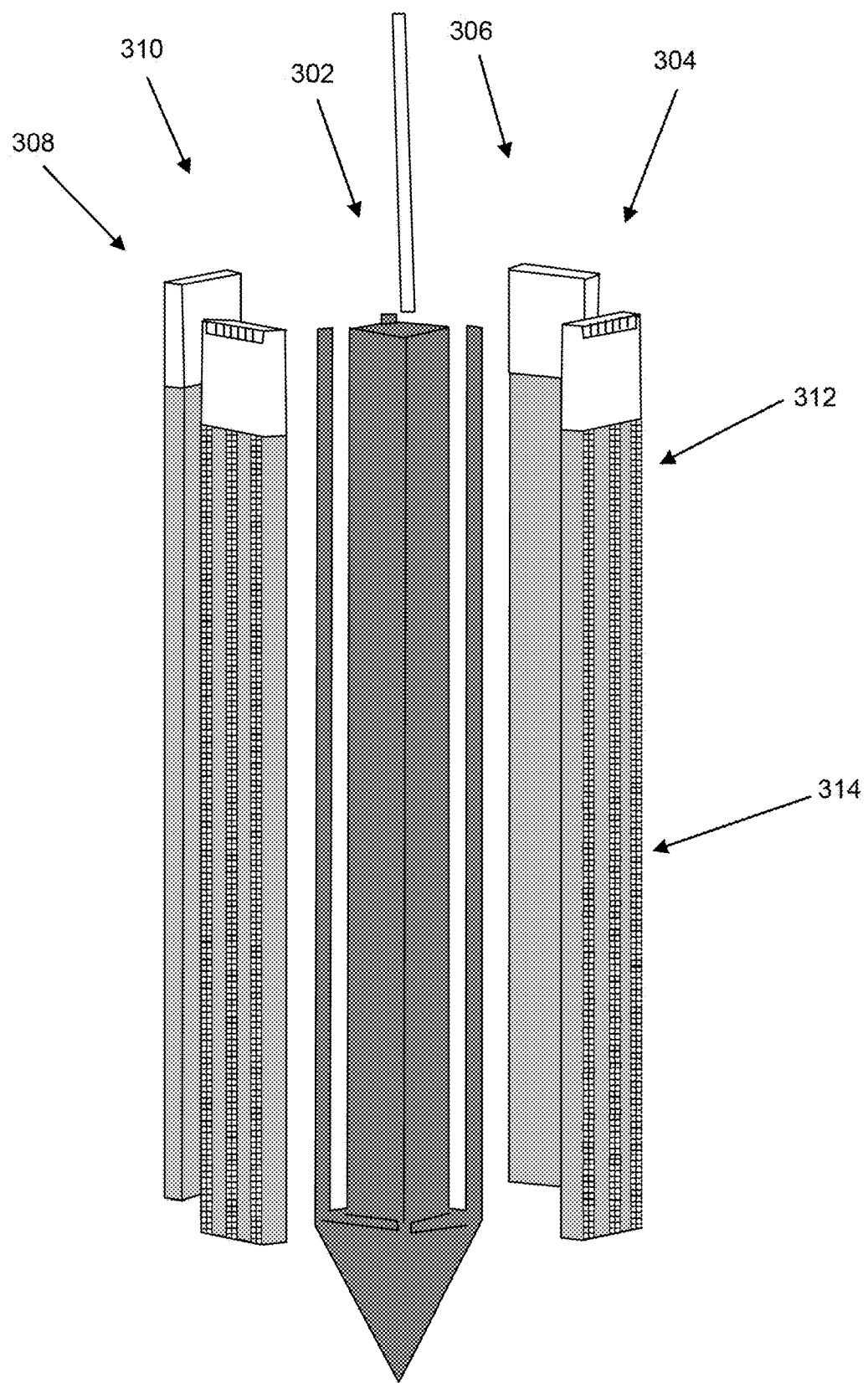
FIG. 3 illustrates another exemplary configuration of a neural probe, consistent with some embodiments of the present disclosure.

FIG. 3 illustrates another exemplary configuration of a neural probe, consistent with some embodiments of the present disclosure. As shown in FIG. 3, the neural probe may include a mold 302 for gluing four sections of micro-electrode arrays 304, 306, 308, and 310 of the neural probe together. Each of the micro-electrode arrays sections 304, 306, 308, and 310 may include its own corresponding application specific integrated circuit for local signal amplification and processing and channels for recording and stimulation. For example, section 304 includes an application specific integrated circuit 312 for local signal amplification and processing and arrays of micro-electrodes 314 for recording and stimulation. Arrays 306, 308, and 310 may include similar structures.

Figure 4:
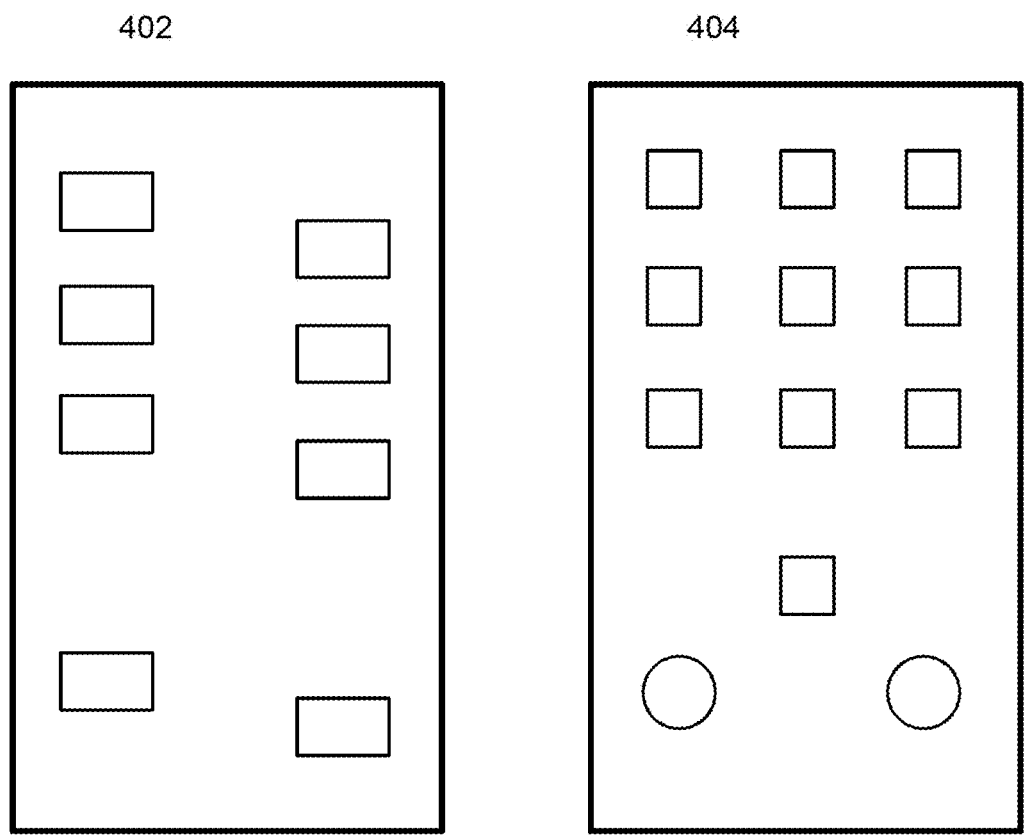
FIG. 4 illustrates various exemplary configurations of an electrode array, consistent with some embodiments of the present disclosure.

FIG. 4 illustrates various exemplary configurations of an electrode array, consistent with some embodiments of the present disclosure. In electrode array 402, the electrodes may be positioned in a staggered configuration from one another, with two rows of electrodes extending parallel to one another. In electrode array 404, the electrodes may be positioned in a side-by-side configuration with three rows of electrodes extending parallel to one another. As shown in electrode array 404, symmetry is not required in the electrode array, as some of the electrodes are shown to be present in some rows, while others are not. Also, in some configurations, electrodes may be rectangular in shape, while in other configurations, they may be square or round in shape, as shown by the bottom row of electrodes in electrode array 404.

Figure 5:
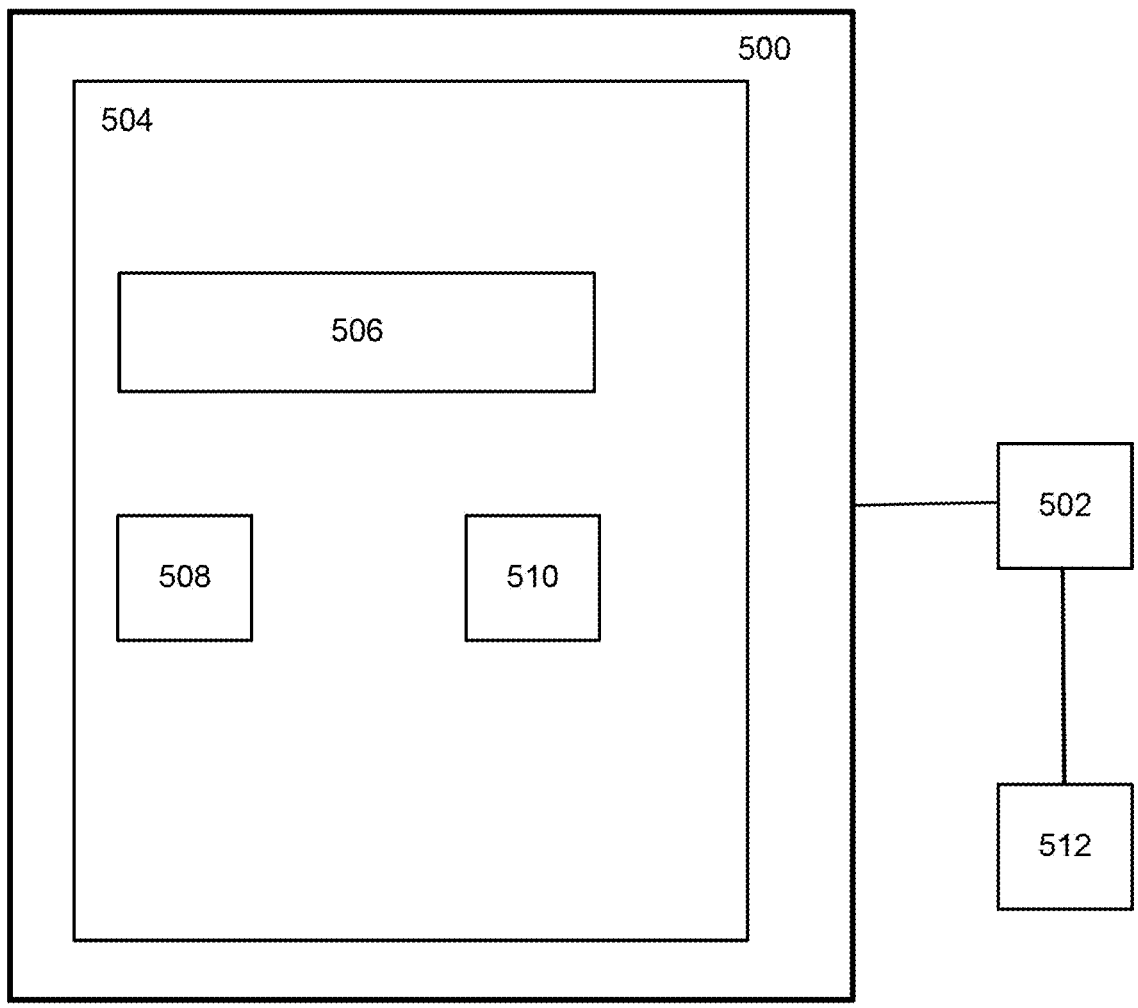
FIG. 5 illustrates elements of an exemplary neural probe, consistent with some embodiments of the present disclosure.

FIG. 5 provides a block-level diagram representative of elements of an exemplary neural probe, consistent with some embodiments of the present disclosure. The neural probe 500 includes at least one signal lead 502 extending from the neural probe 500 and a sensing assembly 504 included on the neural probe 500. The sensing assembly 504 may include a plurality of electrodes 506 positioned on the neural probe 500, wherein one or more of the plurality of electrodes 506 are configured to sense electrical signals generated by one or more neurons in the brain. The sensing assembly 504 may also include at least one amplifier 508 configured to generate at least one amplification signal based on the sensed electrical signals generated by the one or more neurons; at least one multiplexer 510 configured to multiplex at least two amplified signals based on the sensed electrical signals generated by the one or more neurons. Any of the micro-electrodes in the sensing assembly 504 can be switched to a stimulation mode. The signal lead 502 leads to an external processing unit 512 where analogue-to-digital conversion takes place and data is processed. The processing unit also provides power to the probe through the signal lead and contains a stimulus generator for providing stimulation pulses through the micro-electrode arrays.

Some disclosed embodiments may involve systems and methods for providing a sensing/stimulation lead including a plurality of electrodes, where each electrode can be individually operated as both a sensing and a stimulating electrode to generate customized, time-varying stimulation patterns based on sensed signals. For example, a stimulation pattern can be generated by activating one or all of the electrodes in an array, where the activated electrodes are arranged in any desired pattern among the array. In this way, different combinations of electrodes can be activated together to produce different stimulation patterns. For example, in FIG. 10A, electrode 1002 may be used to sense a signal and then administer a stimulation based on that sensed signal.

The disclosed systems and methods are aimed at facilitating deep brain sensing and stimulating in the brain with micrometer spatial resolution. For example, each electrode may be sized at a micron level (e.g., 5-20 microns in diameter) to enable sensing and stimulation of individual neurons, which have cell bodies that are also on the micrometer spatial scale. Each electrode may be configured with an impedance between approximately 1 kOhms and 1 MOhm, to improve signal to noise ratios of sensed signals. The electrodes may be arranged as a single array, dual arrays on opposing sides of the lead, or a plurality of arrays, each on a face of a multi-faceted neural probe shank. The shank may be non-centric, dual-sided, or multi-faceted, to enable stimulation or sensing within a desired geometric volume in deep brain regions.

Disclosed embodiments include a neurostimulator. A neurostimulator refers to any device configured to generate electrical impulses used to stimulate individual neurons, a group of neurons, or white matter tracts. Neurostimulators include invasive and noninvasive approaches that apply electric or electromagnetic energy to specific anatomical targets, such as neurons or the tissue surrounding neurons, to induce neuromodulation of the corresponding neural circuitry. Neurostimulators can be used in various neurostimulation strategies used clinically to modulate disordered circuitry to restore functionality, such as deep brain stimulation (DBS), motor cortex stimulation (MCS), responsive neurostimulation (RNS), spinal cord stimulation (SCS), and vagus nerve stimulation (VNS).

Disclosed embodiments include a neural probe configured for placement within a brain. A neural probe may include any device used to record neural signals, any components used to analyze the recorded signals, or any combination thereof. Neural probes may include microstructures that form a connection between biological neural tissue with physical devices and electronics. A neural probe may include a single or multiple protruding structures or shafts. Each shaft may include recording electrodes, electronic circuitry, interconnecting traces, or a carrier area carrying bonding pads to connect the probes to externally placed electronics. A neural probe may include one or more shafts with minimum thickness to reduce damage to brain tissue when the neural probe is inserted into the brain. The neural probe may incorporate sufficient mechanical strength to survive compression and tension forces during insertion in and retraction from brain tissue.

Placement within a brain may include positioning, arranging, deploying, locating, disposing, installing, stationing, or any other manner of putting a neural probe in contact with any portion of a brain, such as brain tissue. Placing the neural probe within a brain may be desirable to record from or stimulate structures, such as brain regions, neurons, or white matter tracts. As an example, placement within a brain may include implanting a neural probe within the brain. Such implantation may be through surgical or non-surgical means.

Disclosed embodiments include at least one signal lead extending from the neural probe. At least one signal lead extending from the neural probe may include any electrical connection consisting of a length of wire or a metal pad that is configured to connect two locations electrically. A signal lead may include conductive material, such as copper or aluminium. An electrical lead may be coated or tinned. A signal lead may include conductive material surrounded by electrical insulation. As an example, a signal lead may include a copper silkscreen, to improve interference rejection.

Disclosed embodiments include a micro-electrode assembly included on the neural probe in which each electrode can sense or stimulate. A micro-electrode assembly may include any accumulation, aggregation, association, body, cluster, mass, or any other fitting or grouping together of one or more parts configured to sense at least one signal. It may be desirable to provide a micro-electrode assembly on the neural probe to sense signals from one or more regions of brain tissue in close proximity of the neural probe. A micro-electrode assembly included on the probe may include a single electrode assembly provided on one location of the probe. An electrode assembly included on the probe may include two or more electrode assemblies provided on two or more locations of the neural probe. As an example, an electrode assembly may include a first electrode assembly at a distal end of the neural probe and a second electrode assembly placed a given distance away from the first electrode assembly.

Disclosed embodiments include a plurality of dual-role micro-electrodes positioned on the neural probe. In the disclosed embodiments, the dual-role nature of the included electrodes may indicate that any, some, or all electrodes in the electrode assembly may function in both a sensing and stimulating capacity. Thus, in the disclosed embodiments, each of the dual-role electrodes may be configured to sense electrical signals generated by one or more neurons in the brain and to convey to the at least one signal lead one or more amplified and multiplexed sense signals. Further, each of the dual-role micro electrodes may be configured to receive, via the at least one signal lead, a stimulation signal selectively delivered from a stimulus generator. Such dual-role electrodes may be desirable so that the exact location and pattern of stimulation can be determined based on the locally sensed signals, therefore providing a closed-loop recording and stimulation system. A sensing or stimulating function of each such electrode may be configured either automatically or manually by a user. In some instances, an electrode may be automatically configured to sense or stimulate based on a predetermined timing pattern, a sensed environment condition, a measurement, a location, or any other condition associated with the electrode or any other component of the system. In other instances, a user may switch an electrode between a sensing mode and a stimulating mode using a user input device, such as a switch. As an example, a plurality of electrodes may include four electrodes. In this example, all four electrodes may be configured to automatically switch from a sensing to a stimulating mode upon a certain sensing measurement. In another example, two of the four electrodes may be configured to automatically switch from a sensing to a stimulating mode upon a certain sensing measurement, while the remaining two electrodes may be configured to stay in the sensing mode. In another example, all four electrodes will switch from a sensing to a stimulating mode. As illustrated by these examples, any configuration of sensing, stimulating, switching from sensing to stimulating modes, or switching from stimulating to sensing modes is contemplated for use with the disclosed embodiments. In some cases, the disclosed embodiments may include large arrays of microelectrodes (e.g., 64, 128, 256, 506, 1024 or more), and each of the electrodes may be individually controlled to operate in a sensing or stimulation mode (or in a floating mode in which neither sensing or stimulation occurs). Switching between sensing and stimulation modes may be performed automatically or manually at a frequency and amplitude appropriate for a particular application and/or may use any suitable circuitry, including various switches, controllers, etc.

Electrical signals may include any signal generated by any tissue in the brain, including neurons, or components of neurons, such as dendrites or axons. It may be desirable to measure electrical signals using a plurality of electrodes on the neural probe to understand the neural dynamics associated with various diseases associated with deep brain regions, such as Parkinson's disease, essential tremor, or epilepsy. For example, a plurality of electrodes may be used to sense neural signals created by neurons in one or more of the brain structures that make up the basal ganglia or in the thalamus, or any other brain region specifically associated with neurological disease.

In some embodiments, each of the plurality of electrodes comprises at least one conductor. A conductor may include any object or type of material that allows the flow of charge (i.e., electric current) in one or more directions. The composition of a conductor may include aluminum, stainless steel, MP35N, platinum, iridium, gold, silver, titanium, titanium nitride, copper, vanadium, alloys, or other conductive materials or metals known to those of ordinary skill in the art. The number, size, and composition of the one or more conductors may depend on the particular application of the neural probe, as well as the number of electrodes used in the neural probe. The conductor may be insulated from the external surface by insulative material. The insulative material may be of a single composition, or multiple layers of the same or different materials. A conductor may take the form of a surface pad, solid metal wires, drawn-filled-tube, drawn-brazed-strand, stranded wires or cables, ribbon conductors, or other forms known or recognized to those skilled in the art.

In some embodiments, the at least one conductor includes an exposed surface pad comprising a surface area between 25 and 400 square microns. An exposed conductor surface area between 25 and 400 square microns is desirable to efficiently interface with neural tissue at the scales of individual neuronal cells whose size typically ranges between 10 and 50 micrometers in diameter.

In some embodiments, the at least one conductor surface pad comprises gold, titanium nitride, platinum iridium, iridium oxide or some other conductive metal. A gold conductor may be desirable for high electrical conductivity, biocompatibility, and good chemical stability. A gold electrode may also provide high stability in the biological environment while keeping robust structural and steady functional properties over times of usage. A titanium nitride conductor is desirable for biocompatibility, corrosion resistance, and improved wettability for implantation. A platinum iridium or iridium oxide conductor is desirable for biocompatibility, corrosion resistance and improved charge injection capabilities.

In some embodiments, each of the plurality of electrodes has an impedance of between 1 kOhms and 1 MOhm. It is desirable for the electrodes to have an impedance within a range, such as between 1 kOhms and 1 MOhm, because the electrode impedance may affect the signal to noise ratio in the measured electrical signals and therefore the ability to detect action potentials from individual neurons.

In some embodiments, the sensing assembly comprises circuitry operable to switch each of the plurality of micro electrodes between a sensing mode and a stimulation mode. A sensing or stimulating function of each such electrode may be configured either automatically or manually by a user. In some instances, an electrode may be automatically configured to sense or stimulate based on a timing, an environment, a measurement, a location, or any other condition associated with the electrode or any other component of the system. In other instances, a user may switch an electrode between a sensing mode and a stimulating mode using a user input device, such as a switch. As an example, a plurality of electrodes may include four electrodes. In this example, all four electrodes may be configured to automatically switch from a sensing to a stimulating mode upon a certain sensing measurement. In another example, two of the four electrodes may be configured to automatically switch from a sensing to a stimulating mode upon a certain sensing measurement, while the remaining two electrodes may be configured to stay in the sensing mode. In another example, all four electrodes will switch from sensing to a stimulating mode. As illustrated by these examples, any configuration of sensing, stimulating, switching from sensing to stimulating modes, or switching from stimulating to sensing modes is contemplated for use with the disclosed embodiments.

In some embodiments, the plurality of dual-role micro electrodes is arranged in at least one array. An array refers to any configuration of a plurality of electrodes. Arranging the plurality of electrodes in at least one array is desirable for allowing the placement of multiple electrodes at once rather than individually, the ability to select different recordings sites within the array, the ability to simultaneously receive data from multiple sites, and the ability to stimulate from a plurality of electrode sites on the array. In some examples, the at least one array comprises at least one rectangular array for an equally spaced and dense measurement area. For example, the array may be a 20 by 30 array of electrodes. In other examples, the at least one array comprises at least one hexagonal array for improved measurement using a single array in unconventionally shaped brain regions.

In some embodiments, the neural probe comprises at least one facet on which at least some of the plurality of micro electrodes are disposed. A facet refers to any flat surface on an object. For example, a single facet may be one side of a two-sided substrate, wherein the plurality of electrodes may be disposed on that one side of the substrate. As another example, some of the plurality of electrodes may be disposed on one side of the substrate, while the remaining electrodes may be disposed on the other side of the neural probe. It may be desirable to use at least one facet on which at least some of the plurality of electrodes are disposed to allow measurement of opposite sides of the neural probe in a neural region.

In some embodiments, the neural probe comprises two facets, including a first facet and a second facet on opposing faces of the neural probe, on which at least some of the plurality of micro-electrodes are disposed. For example, a first facet may be one side of a two-sided substrate, and a second facet may be another side of the two-sided substrate. In this example, some of the plurality of electrodes may be disposed on the first facet of the substrate, while the remaining electrodes may be disposed on the second facet of the electrode. It may be desirable to use two facets, including a first facet and a second facet on opposing faces of the neural probe, on which at least some of the plurality of electrodes are disposed to allow measurement of opposite sides of the neural probe in a neural region.

In some embodiments, the neural probe comprises three facets on which at least some of the plurality of micro-electrodes are disposed. In some examples, the three facets are arranged such that the neural probe comprises a triangular cross-section. It may be desirable to use three facets on which at least some of the plurality of electrodes are disposed to allow measurement in three dimensions in a brain region.

In some embodiments, the neural probe comprises four facets on which at least some of the plurality of micro-electrodes are disposed. In some examples, the four facets are arranged such that the neural probe comprises a quadrilateral cross-section. It may be desirable to use three facets on which at least some of the plurality of electrodes are disposed to allow improved measurement in three dimensions in a brain region.

In some embodiments, the neural probe is non-centric. Non-centric may refer to a shape having a non-circular profile in any dimension, such as a cross-section. In some examples, the neural probe may be non-centric in the form of a probe with a square or rectangular cross-section. In other examples, the probe may be non-centric in the form of a probe with a triangular cross-section.

In some embodiments, the one or more sense signals are amplified and multiplexed by electronic circuitry local to the neural probe. Amplification may include any increase of an amplitude, in terms of voltage or current, of a time-varying signal by a given factor. Amplification may be performed using an amplifier, which may include any electric device configured to increase the power or intensity of a signal, such as a time-varying voltage or current. An amplifier may include any two-port electronic circuit that configured to use electric power from a power supply to increase an amplitude of a signal applied to its input terminals, producing a proportionally greater amplitude signal at its output. It may be desirable to amplify a signal to increase an amplitude of a small input signal to a level that can be perceived or analyzed by other electronic circuits. As an example, amplification may include increasing the intensity of a voltage signal by a factor of three.

Amplification by an amplifier local to neural probe may include any increase of an amplitude of a time-varying signal at a location that is close in proximity to the source of the time-varying signal, which may be the neural probe. It may be desirable to perform local amplification to reduce significant attenuation of the small sensed signals along the length of the conductors and signal leads. For example, local amplification of a signal produced at position A on the neural probe may be performed by placing an amplifier circuit in close proximity to position A on the neural probe, such as one millimeter or less from position A, as opposed to twenty or more millimeters from position A.

In some embodiments, each of the plurality of micro-electrodes is configured to sense electrical signals generated by neurons located within a distance of up to 200 microns. It may be desirable to configure the plurality of electrodes to sense electrical signals generated by neurons located within a range of up to 200 microns to sense electrical signals from individual neurons within a small localized brain region. The amplitudes of action potentials are in the microvolt range and the amplitudes of these small signals rapidly attenuate with distance. Thus, designing electrode dimensions on the micrometer scale will allow for measurements of action potentials of nearby individual neurons, in addition to sensing electrical signals defined as local field potentials, which represent the aggregated electrical activity of both far away and local neurons, as well as synaptic potentials carried by white matter tracts.

A stimulation signal may refer to any signal that produces electrical changes in one or more neurons. The electrical impulses may modulate abnormal neural activity locally and in brain areas connected to the local target area. The frequency, amplitude and pulse width of the stimulating signal received by the dual-role electrodes may be programmed using external devices and software algorithms. Stimulating one or more neurons in the brain using the one or more plurality of micro-electrodes may involve using a dedicated current source for each electrode contact, or a single current or voltage source that is shared by different electrode contacts. The configuration of the plurality of electrodes used for stimulation may vary in terms of the spacing between electrode contacts as well as the number and shape of electrode contacts. Monopolar stimulation may involve current being directed from a location outside of the brain, such as from the power source to the electrode contact or vice versa. Bipolar stimulation may involve current flowing between electrode contacts, with at least one functioning as an anode and one as a cathode. Interleaving stimulation may involve the alternation of different stimulation settings. Using directional stimulation, current may be directed or shaped based on local anatomy, clinical symptoms, or locally recorded neural signals. One type of stimulation of one or more neurons in the brain using the one or more plurality of electrodes may include deep brain stimulation, to improve disease symptoms, such as those associated with Parkinson's disease.

In some embodiments, the at least one neural probe includes a plurality of conductors, such that each of the plurality of dual-role micro-electrodes is associated with a single conductor configured to both carry sensed signals from and to deliver a stimulation signal to one of the plurality of dual-role micro-electrodes. It may be desirable for each of the plurality of dual-role electrodes to be associated with a single conductor configured to both carry sensed signals from and to deliver a stimulation signal to one of the plurality of dual-role electrodes to reduce the amount of wires incorporated in the neural probe. Reducing the number of wires in the neural probe reduces the overall width and size of the neural probe and may improve the ease of insertion of the neural probe as well as minimizing neuronal damage.

In some embodiments, the at least one neural probe includes a plurality of conductors, such that each of the plurality of dual-role micro-electrodes is associated with at least two conductors, wherein a first of the at least two conductors is configured to carry sensed signals from a particular one of the plurality of dual-role electrodes, and a second of the at least two conductors, different from the first of the at least two conductors, is configured to deliver a stimulation signal to the particular one of the plurality of dual-role electrodes. It may be desirable for each of the plurality of dual-role electrodes to be associated with a single conductor configured to carry sensed signals from and another conductor to deliver a stimulation signal to one of the plurality of dual-role electrodes to improve signal quality and reduce noise by limiting each conductor to a single type of signal: either sensed or stimulation.

A stimulus generator may include electrical circuitry responsive to programming signals that selectively activates a plurality of the dual-role micro-electrodes, wherein at least one electrode in the plurality of activated the dual-role electrodes functions as a cathode, and wherein at least one electrode in the plurality of activated the dual-role electrodes functions as an anode, whereby stimulus current flows from the at least one activated anodic electrode to the at least one activated cathodic electrode, resulting in bipolar stimulation. Alternatively, a single of the dual-role electrodes is used as cathode and the stimulus generator itself functions as the anode, resulting in monopolar stimulation. Or, in another example of monopolar stimulation, a single of the dual-role electrodes is used as the anode and the stimulus generator itself functions as the cathode. The stimulus generator may include control circuitry that generates programming signals adapted to control the stimulus generator. Selective delivery of a stimulation signal may involve the use of control logic that continuously activates selected ones of the plurality of dual-role electrodes in response to input signals, such as from user interaction with an input device, feedback signals based on the sensed electrical signals, or another signal or component of the neurostimulator system, whereby stimulus current is selectively redistributed among cathodic and anodic electrodes as directed by the input signals. The electrical circuitry within the stimulus generator may activate the selected electrodes by forcing a prescribed current to flow into (a current sink) a cathodic electrode, by forcing a prescribed current to flow from (a current source) an anodic electrode, by causing a prescribed positive voltage to be applied to an anodic electrode, by causing a prescribed negative voltage to be applied to a cathodic electrode, or by combinations of the above.

Figure 6:
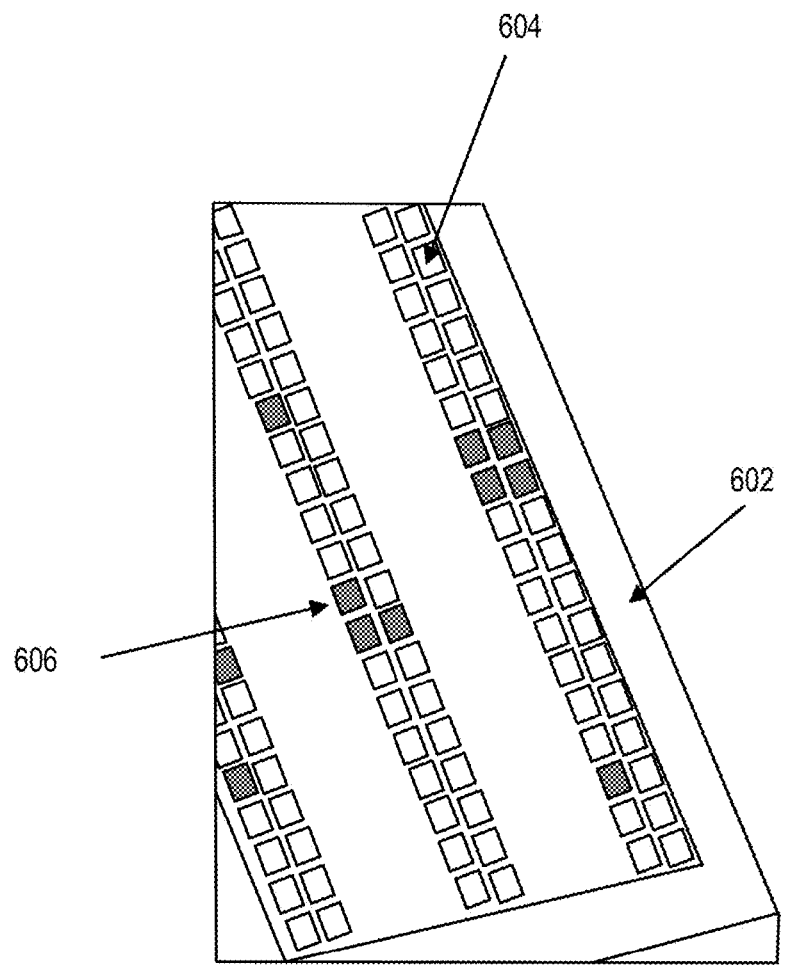
FIG. 6 illustrates an example of selectively activated electrodes, consistent with some embodiments of the present disclosure.

FIG. 6 illustrates an example of selectively activated electrodes, consistent with some embodiments of the present disclosure. As shown in FIG. 6, the neural probe 602 may include a plurality of electrodes, such as electrode 604 and 606. Each of the plurality of electrodes may be selectively activated for either sensing or stimulating functions. In FIG. 6, electrode 604 is not activated for stimulating. However, electrode 606 is activated for stimulating.

Figure 7:
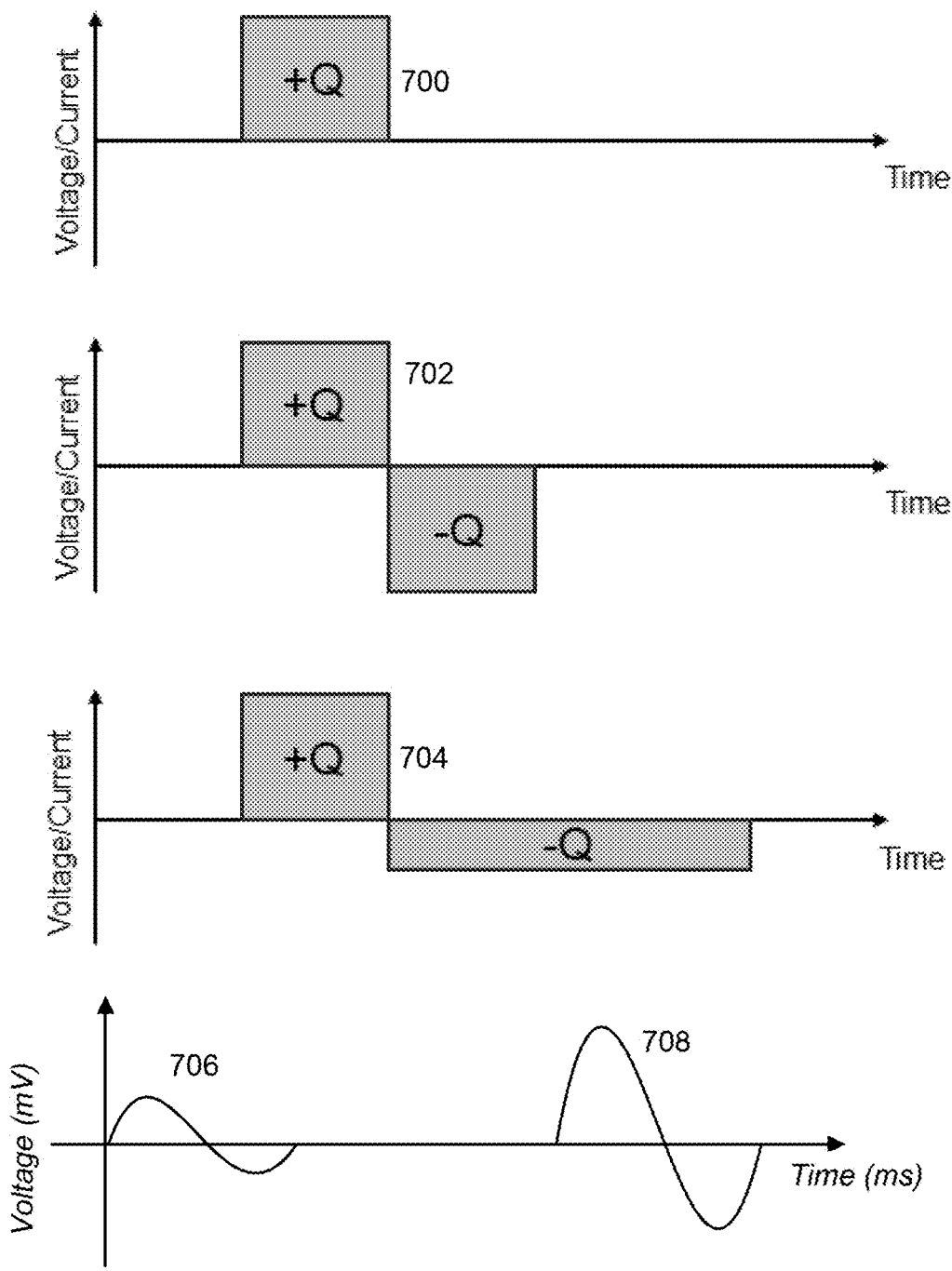
FIG. 7 illustrates selective activation of an exemplary neurostimulator, consistent with some embodiments of the present disclosure.

FIG. 7 illustrates selective activation of an exemplary neurostimulator, consistent with some embodiments of the present disclosure. As shown in FIG. 7, selective activation of the electrodes may involve selective application of a voltage or a current to affect a desired stimulation function. For example, at different time intervals biphasic, charge balanced waveforms of differing amplitudes may be selectively applied to one or more electrodes associated with the neurostimulator. In some cases, the stimulation signals may be applied to groups of micro-electrodes arranged in a predetermined pattern to generate a desired stimulation pattern within brain tissue in regions adjacent to the neural probe. A stimulation waveform can be monophasic, or biphasic and charge balanced with sometimes the discharge phase being longer in time, but lower in amplitude than the charge phase. In the example shown in FIG. 7, the stimulation waveform may be monophasic 700, bi-phasic 702, or bi-phasic with a slower discharge 704. In this example, a recorded waveform may visualize the process of recording a biomarker at 706 and modulating the recorded biomarker signal at 708.

In some embodiments, stimulation signals selectively delivered from the signal generator to corresponding ones of the plurality of electrodes cause activation of at least some of the plurality of micro-electrodes according to a selected stimulation pattern. The selected stimulation pattern may include activation of a first electrode and activation of at least a second electrode, different from the first electrode, during an overlapping time-period. The selected stimulation pattern may be time-varying. The selected stimulation pattern may be amplitude-varying. The stimulation pattern may be selected based on at least one characteristic associated with the one or more sense signals. The at least one characteristic may include a magnitude of the one or more sense signals. The at least one characteristic may include a frequency associated with the one or more of sense signals. The at least one characteristic may include a spatial distribution relative to the neural probe of the one or more sense signals.

In some embodiments, stimulation signals selectively delivered from the signal generator to corresponding ones of the plurality of electrodes cause activation during a first time period of a first set of the plurality of electrodes to provide a first stimulation pattern and cause activation, during a second time period different from the first time period of a second set of the plurality of electrodes to provide a second stimulation pattern. In some examples, the first set of the plurality of electrodes and the second set of the plurality of electrodes share at least one electrode in common. In other examples, the first set of the plurality of electrodes and the second set of the plurality of electrodes share no electrodes in common. It may be desirable to cause activation of the electrodes during different time periods to modulate stimulation therapy based on a relevant time for an associated condition of the patient, such as Parkinson's disease or epilepsy. It may also be desirable to cause activation of the electrodes during different time periods to limit the amount of electrical stimulation delivered in a given period of time, thereby mitigating a risk of tissue damage or to limit power usage.

In some embodiments, in response to a delivered stimulation signal, each of the plurality of electrodes is configured to cause emission of an electrical field extending into the brain by at least 50 microns up to hundreds of microns. It may be desirable to configure in response to a delivered stimulation signal, each of the plurality of electrodes to cause emission of an electrical field extending into the brain by at least 50 microns to stimulate only locally in the targeted brain region, not beyond it, and with high spatial precision. Thus, using a stimulating radius up to 50 microns may allow the system to improve the granularity of stimulation delivered to surrounding neural tissue. As an example, the plurality of electrodes may be configured to cause emission of an electrical field extending into the brain by 400 microns. As another example, the plurality of electrodes may be configured to cause emission of an electrical field extending into the brain by 50 microns. In this example, different stimulation signals may be applied even to the cell body of a single neuron. With the disclosed embodiments, the electric fields generated by groups of electrodes may be contained within a precise region (e.g., within a 50-micron zone, in some cases). In other cases, larger fields may be generated to produce more widespread stimulation (e.g., zones of 100 microns, 200 microns, 300 microns, or more). The described electrode arrangements and electrode control capabilities may provide the ability to precisely stimulate brain tissue only within a targeted zone or region, whether that zone or region is small (e.g., less than 100 microns in diameter) or larger (e.g., greater than 100 microns in diameter).

In some embodiments, the neurostimulator further comprises a power assembly configured to be located on the skull of the brain that can be charged via electrodynamic wireless power transmission, inductive power transmission, or resonant power coupling. A power assembly may include a configuration of mechanical connections and conductive material arranged in such a way as to provide power or signal distribution to one or more components of the system, such as to stimulate one or more neurons using the plurality of electrodes. The power assembly may include a power source. Any power source can be used including, for example, a battery such as a primary battery or a rechargeable battery. Examples of other power sources include super capacitors, nuclear or atomic batteries, mechanical resonators, infrared collectors, thermally powered energy sources, flexural powered energy sources, bioenergy power sources, fuel cells, bioelectric cells, osmotic pressure pumps, and other similar devices. It may be desirable to configure the power assembly to be located on a skull of the brain to limit the number of system components inserted within the brain tissue. By locating the power assembly on the skull, a risk of damage to brain tissue caused, for example, by battery malfunction or failure, may be avoided.

Electrodynamic wireless power transmission may deliver electrical power from a transmitter coil to a compact electromechanical receiver over a range of distances using low-amplitude, low-frequency magnetic fields. An electrodynamic wireless power transfer system may use a receiver with a mechanically resonating or rotating permanent magnet. When subjected to a time-varying magnetic field, the mechanical motion of the resonating magnet may be converted into electricity by one or more electromechanical transduction schemes (e.g., electromagnetic/induction, piezoelectric, or capacitive). Compared to other wireless power transfer schemes, electrodynamic wireless power transfer systems leverage low-frequency magnetic fields (i.e., less than 1 kHz), which safely pass through conductive media and have higher human field exposure limits. Thus, it may be desirable to use electrodynamic wireless power transfer to wirelessly recharge biomedical devices, such as a neural probe. Inductive power transmission may involve power being transferred between coils of wire by a magnetic field. Inductive power transfer systems have many advantages towards wired solutions, such as the elimination of wires or the omission of open contacts. Thus, inductive power transmission offers added value in applications such as powering a neural probe. Resonant power coupling may involve the use of coils capacitively loaded to form a tuned LC resonating at a common frequency, which allows for transmission of significant power over wider ranges, which may be desirable for applications such as powering a neural probe.

Figure 8:
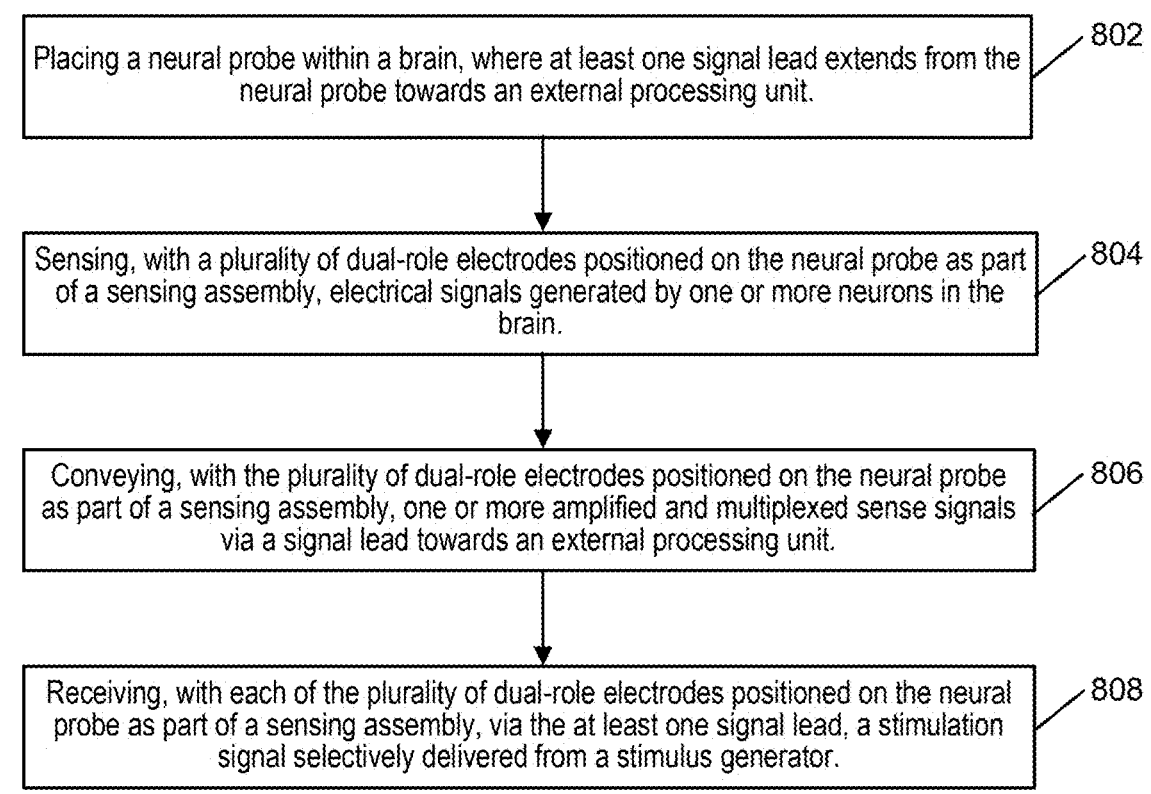
FIG. 8 illustrates a flowchart of a method for using a neurostimulator, consistent with some embodiments of the present disclosure.

FIG. 8 illustrates a flowchart of a method 800 for using a neural interface, consistent with some embodiments of the present disclosure. Method 800 may include a step 802 of placing a neural probe within a brain, wherein at least one signal lead extends from the neural probe towards a processing unit with a power source and stimulus generator. Method 800 may include a step 804 of sensing, with a plurality of dual-role micro-electrodes positioned on the neural probe as part of a sensing assembly, electrical signals generated by one or more neurons in the brain. Method 800 may include a step 806 of conveying, with the plurality of dual-role micro-electrodes positioned on the neural probe as part of a sensing assembly, one or more sense signals generated based on the sensed electrical signals to the external processing unit via at least one signal lead. Method 800 may include a step 808 of receiving, with each of the plurality of dual-role micro-electrodes positioned on the neural probe as part of a sensing assembly, via the at least one signal lead, a stimulation signal selectively delivered from a stimulus generator.

Local Amplification of Sensed Signals from a DBS Electrode Array

Some disclosed embodiments may involve systems and methods for recording electrical signals from individual neurons (or groups of neurons) or from other sources in deep brain regions. The disclosed systems include a micro-sensing assembly comprising small electrodes capable of both stimulating small, targeted regions and sensing electrical signals emanating from those regions. An important aspect in enabling sensing from deep brain regions is the system's ability to effectively transfer sensed signals from the deep brain regions to a location outside of a subject's body. Sensed signals from neurons in the brain may have small amplitudes. Signal attenuation associated with transferring the sensed signals away from deep brain regions can degrade the signals of interest to a point where accurate sensing and signal analysis is not possible.

The disclosed systems are aimed at addressing the attenuation-based challenges associated with transmitting signals out of deep regions of the brain. For example, the disclosed systems may include one or more local amplifiers to boost the amplitude of signals sensed by a deep brain sensor. As a result, the disclosed systems may offer significantly improved signal-to-noise ratios relative to sensed signals transferred out of the subject's body. Local amplification may also allow for signal processing schemes tailored to individual electrodes or groups of electrodes, as opposed to a globalized signal processing scheme. Multiplexing of amplified signals from individual electrodes allows for a single or a few output wires carrying the signals out of the brain to a processing unit.

Disclosed embodiments include a system for local amplification and multiplexing of signals sensed from deep brain regions. Amplification may include any increase of an amplitude, in terms of voltage or current, of a time-varying signal by a given factor. Amplification may be performed using an amplifier, which may include any electric device configured to increase the power or intensity of a signal, such as a time-varying voltage or current. An amplifier may include any two-port electronic circuit that is configured to use electric power from a power supply to increase an amplitude of a signal applied to its input terminals, producing a proportionally greater amplitude signal at its output. It may be desirable to amplify a signal to increase an amplitude of a small input signal to a level that can be perceived or analyzed by other electronic circuits. As an example, amplification may include increasing the intensity of a voltage signal by a factor of three.

Local amplification may include any increase of an amplitude of a time-varying signal at a location that is close in proximity to the source of the time-varying signal. It may be desirable to perform local amplification to reduce the amplification of additional noise between the source of the input signal and the amplifier. For example, local amplification of a signal produced at position A may be performed by placing an amplifier circuit in close proximity to position A, such as 1 millimeter or less from position A, as opposed to twenty millimeters or more from position A.

Multiplexing may include any method by which multiple analog signals are combined into one signal over a shared medium, such as a physical transmission medium. An example of a physical transmission medium is a cable, but other transmission media are also contemplated. The multiplexed signal is transmitted over a communication channel such as a cable. The multiplexing divides the capacity of the communication channel into several logical channels, one for each message signal or data stream to be transferred. A reverse process, known as demultiplexing, extracts the original channels on the receiver end. Multiplexing may be beneficial to send more than one signal over a single medium, thereby using the bandwidth of the medium more efficiently. As an example, multiplexing may be applied to share the bandwidth of one link across three input lines.

Signals may include any functions that convey information about a phenomenon, such as a physiological phenomenon. Signals may refer to any time-varying voltage, current, or electromagnetic waves that carry information. Signals may be generated by transducers, such as an electrode. Signals may also be provided by other input devices, such as processors or servers. As an example, signals may include a neural signal recorded from a micro-electrode array on a neural probe.

Deep brain regions may include any one or combination of subcortical structures with clinical importance in diseases. Deep brain regions include regions in the diencephalon, such as the hypothalamus, the thalamic nuclei, the subthalamic nuclei, regions in the mesencephalon or midbrain such as the substantia nigra, and tectum, regions in the rhombencephalon or hindbrain such as the pons and cerebellum, or any part of the limbic system, such as the hippocampal formation and amygdala. Sensing signals from deep brain regions may be desirable for helping clinicians directly identify deep brain structures relevant to present and future medical applications, such as diagnosis and treatment of diseases associated with deep brain regions. In one example, deep brain regions may include the thalamus since the thalamus is associated with epileptic disorders. In another example, deep brain regions may include nuclei in the basal ganglia since these regions are associated with Parkinson's disease.

Disclosed embodiments include a neural probe configured for placement within a brain. A neural probe may include any device used to record neural signals, any components used to process or analyze the recorded signals, or any combination thereof. Neural probes may include micron sized structures that create an interface between biological neural tissue with physical devices and electronics. A neural probe may include a single or multiple protruding structures or shafts. Each protruding structure or shaft may be thin, to reduce damage to neuronal tissue. Each shaft may include sensing sites, interconnecting traces, or a carrier area carrying bonding pads to connect the probes to electronics. Minimizing the size of the neural probe is also desirable to efficiently interface neural tissue at the scales of neurons whose size typically ranges between 10 and 50 micrometers in diameter. The neural probe may include a shaft wide enough to hold a plurality of dual role micro-electrode sites to measure and stimulate neural electrical activity at different depths and locations and route interconnect traces to connect the recording sites to bonding pads. The neural probe may incorporate sufficient mechanical strength to survive compression and tension forces during insertion in and retraction from brain tissue.

Placement within a brain may include positioning, arranging, deploying, locating, disposing, installing, stationing, or any other manner of putting a neural probe in contact with any portion of a brain, such as brain tissue. Placing the neural probe within a brain may be desirable to record from or stimulate tissue, such as brain regions or neurons. As an example, placement within a brain may include implanting a neural probe within the brain. Such implantation may be through surgical or non-surgical means.

Disclosed embodiments include at least one signal lead extending from the neural probe. At least one signal lead extending from the neural probe may include any electrical connection consisting of a length of wire or a metal pad that is configured to connect two locations electrically. A signal lead may include conductive material, such as copper. An electrical lead may be coated or tinned. A signal lead may include conductive material surrounded by electrical insulation. As an example, a signal lead may include a copper silkscreen, to improve interference rejection.

In some embodiments, the at least one signal lead includes one or more electrical conductors. An electrical conductor may include any object or type of material that allows the flow of charge (i.e., electric current) in one or more directions. The composition of a conductor may include aluminum, stainless steel, MP35N, platinum, gold, silver, copper, vanadium, alloys, or other conductive materials or metals known to those of ordinary skill in the art. The number, size, and composition of the one or more conductors may depend on the particular application for the signal lead, as well as the number of electrodes on the neural probe. The conductors may be insulated from the external surface of the signal lead by insulative material. The insulative material may be of a single composition, or multiple layers of the same or different materials. A conductor may take the form of solid wires, drawn-filled-tube, drawn-brazed-strand, stranded wires or cables, ribbon conductors, or other forms known or recognized to those skilled in the art. As an example, the at least one signal lead may include two electrical conductors composed of aluminum.

In some embodiments, the at least one signal lead has a length of at least 40 millimeters. In some embodiments, the at least one signal lead has a length of at least 50 millimeters. In some embodiments, the at least one signal lead has a length of at least 60 millimeters. In some embodiments, the at least one signal lead has a length of at least 70 millimeters. In some embodiments, the at least one signal lead has a length of at least 80 millimeters. For applications in which electrodes are used to sense electrical signals from neurons in the brain, it may be desirable to minimize or eliminate excess signal lead length. This is because excess lead length may be uncomfortable for a patient in which the signal lead is implanted or may cause lead abrasion due to activity such as rubbing against the skull.

Disclosed embodiments include a sensing assembly included on the neural probe. A sensing assembly may include any accumulation, aggregation, association, body, cluster, mass, or any other fitting or grouping together of one or more parts configured to sense at least one signal. It may be desirable to provide a sensing assembly on the neural probe to sense signals from one or more regions of brain tissue in the vicinity of the neural probe. A sensing assembly included on the probe may include a single sensing assembly provided on one location of the probe. A sensing assembly included on the probe may include two or more sensing assemblies provided on two or more locations of the sensing probe. As an example, a sensing assembly may include a first sensing assembly at a distal end of the neural probe and a second sensing assembly placed a given distance away from the first sensing assembly.

Disclosed embodiments include a plurality of dual-role micro-electrodes positioned on the neural probe, wherein one or more of the plurality of electrodes are configured to sense electrical signals generated by one or more neurons in the brain. A plurality of electrodes may include two or more conductors through which electricity enters or leaves an object, substance, or region. The plurality of electrodes may include metals such as gold, platinum, iridium oxide, titanium nitride or other similar materials. The plurality of electrodes may be insulated by materials such as polyimide, epoxy, polyparaxylylene, parylene, acrylics, alumina, silicon, silicon nitride, or other similar materials. As an example, a plurality of electrodes may include two conductors placed a certain distance X from one another on the neural probe. As another example, a plurality of electrodes may include two conductors placed on opposite faces of a two-dimensional neural probe. As another example, multiple facets including a plurality of electrodes may be combined into a multi-dimensional structure.

Electrical signals may include any signal or information created by any tissue in the brain, including neurons, or components of neurons, such as dendrites or axons. It may be desirable to measure electrical signals using a plurality of electrodes on the neural probe to understand the neural dynamics associated with various diseases associated with deep brain regions, such as epilepsy or Parkinson's disease. For example, a plurality of electrodes may be used to sense neural signals created by neurons in the nuclei of the basal ganglia.

In some embodiments, one or more of the plurality of electrodes are configured to provide electrical stimulation resulting in an electric field in local neural tissue in the brain. Generating an electric field in the neural tissue may include producing electrical impulses in one or more neurons or axonal fibers. Generating an electric field in neural tissue may also prevent electrical impulses in one or more neurons or axonal fibers. The electrical impulses may modulate abnormal neural activity. The electric field may also affect certain other cells and chemicals within the brain. The frequency, amplitude and pulse width of the stimulating current delivered to the plurality of electrodes may also be programmed using external electrical components. Stimulating one or more neurons in the brain using the one or more plurality of electrodes may involve using a dedicated current or voltage source for each electrode contact, or a single current or voltage source that is shared by different electrode contacts. The configuration of the plurality of electrodes used for stimulation may vary with respect to the spacing between electrode contacts as well as the number and shape of electrode contacts. Greater contact spacing or grouping of electrodes for the purpose of stimulation expands the size of the electric field and therefore the range of neural targets, whereas smaller contact spacing and the use of individual electrodes for the purpose of stimulation facilitates more precise stimulation control. Monopolar stimulation may involve current being directed from a battery to the electrode contact or vice versa. Bipolar stimulation may involve current flowing between electrode contacts, with at least one functioning as an anode and one as a cathode. Interleaving stimulation may involve the alternation of different stimulation settings. Using directional stimulation, electrical fields may be directed or shaped on the basis of local anatomy or clinical symptoms. One type of stimulation of one or more neurons in the brain using the one or more plurality of electrodes may include deep brain stimulation, which can be used to improve disease symptoms, such as those associated with Parkinson's disease.

In some embodiments, the plurality of micro-electrodes includes one or more dual-role electrodes selectively configurable to stimulate one or more neurons in the brain or to sense electrical signals generated by one or more neurons in the brain. Using dual-role micro-electrodes selectively configurable to stimulate one or more neurons in the brain or to sense electrical signals generated by one or more neurons in the brain may be desirable to limit the overall size of the system. In addition, the ability to stimulate through even one individual micro-electrode allows for spatial precision of stimulation at the micrometer scale. Furthermore, stimulation through micro-electrodes requires less power, thereby reducing overall power consumption of the system. A sensing or stimulating function of each such electrode may be configured either automatically or manually by a user. In some instances, an electrode may be automatically configured to sense or stimulate based on a timing, an environment, a measurement, a location, or any other condition associated with the electrode or any other component of the system. In other instances, a user may switch an electrode between a sensing mode and a stimulating mode using a user input device, such as a switch. As an example, a plurality of electrodes may include four electrodes. In this example, all four electrodes may be configured to automatically switch from a sensing to a stimulating mode upon a certain sensing measurement. In another example, two of the four electrodes may be configured to automatically switch from a sensing to a stimulating mode upon a certain sensing measurement, while the remaining two electrodes may be configured to stay in the sensing mode. As illustrated by these examples, any configuration of sensing, stimulating, switching from sensing to stimulating modes, or switching from stimulating to sensing modes is contemplated for use with the disclosed embodiments.

In some embodiments, the one or more of the plurality of electrodes are configured to sense electrical signals from individual neurons, or a plurality of individual neurons, that are located within an approximately 200-micron radius from an area of the neural probe on which the one or more of the plurality of electrodes are located. It may be desirable to configure the one or more of the plurality of electrodes to sense electrical signals from individual neurons to establish the involvement of individual neurons in both healthy and pathological disease states. The cell body of individual neurons, while varying between brain regions, is generally between 10-80 microns in diameter. To sense the electrical activity of individual neurons, the dimensions of the electrodes must be on the same order of magnitude. Thus, using electrode dimensions of between 10-80 microns may allow the system to improve the granularity of measurement to such a degree that recordings from individual neurons become feasible. As an example, the one or more of the plurality of electrodes may be configured to sense electrical signals from small neurons with a 10-micron diameter from an area of the neural probe on which the one or more of the plurality of electrodes are located. In this example, the sensing assembly will be measuring electrical signals in the surrounding neural space at a spatial resolution that is sufficient to record from individual neurons.

Disclosed embodiments include at least one amplifier configured to generate at least one amplification signal based on the sensed electrical signals generated by the one or more neurons. An amplifier may include any device configured to amplify and condition bioelectric signals that arise from the nervous system, both central and peripheral, into an amplified signal called an amplification signal. Neural signals are characterized by their signal bandwidth (i.e., frequency content) and amplitude. As such, neural signals are generally smaller in amplitude than other biological electrical signals, spanning low-(below 100 Hz) to mid-range (tens of kHz) frequencies. Thus, the amplifier may be configured to address high-gain and low-noise characteristics. As an example, the plurality of electrodes may sense electrical signals generated by the one or more neurons, such as single unit activity or action potentials. In this example, the electrical signals may first be pre-amplified by a front-end amplifier. The front-end amplifier in this example may have the lowest input-referred noise and higher gain than the subsequent stages, as the referred-to-input noise of all subsequent stages may be referred back to the electrodes through the gain of this amplifier. In this example, the subsequent amplifier stages may include one or more cascaded amplifier configurations to provide additional gain, limit the signal bandwidth (to filter noise), and drive external loads to other devices, such as an input of a multiplexer.

In some embodiments, the at least one amplifier includes at least one of a low-noise operational transconductance amplifier, a Miller operational transconductance amplifier, a current mirror operational transconductance amplifier, or a differential self-biased operational transconductance amplifier. Amplification using a low-noise operational transconductance amplifier, a Miller operational transconductance amplifier, a current mirror operational transconductance amplifier, a differential self-biased operational transconductance amplifier, or any other similar amplifiers may be desirable for improving noise-power efficiency. It may also be desirable to use such amplifier configurations to minimize a large electrode-DC-offset (EDO) with a high power-supply rejection ratio (PSRR) to prevent saturation. In one example, a fully differential two or three-stage topology may be included as an operational transconductance amplifier due to its simple and robust architecture. In this example, such an amplifier topology may provide a high DC gain, wide output voltage swing, and good linearity.

In some embodiments, the at least one amplifier is configured to vary a gain associated with the at least one amplification signal based on at least one characteristic of the sensed electrical signals. A gain associated with the at least one amplification signal may include any ability of a two-port circuit (such as an amplifier) to increase the power or amplitude of a signal from the input to the output port by adding energy converted from some power supply to the signal. A gain may refer to the mean ratio of the signal amplitude or power at the output port to the amplitude or power at the input port. It may be desirable to vary a gain associated with the at least one amplification signal based on at least one characteristic of the sensed electrical signals in order to modulate the amplification signal in accordance with any physiologically significant events or characteristics, as indicated by the characteristic. For example, the at least one amplifier may be configured to vary a gain associated with the at least one amplification signal based on a noise of the sensed electrical signals. In this example, the amplifier may be configured to increase the gain when noise is low and decrease the gain when noise is high, in order to prevent noise amplification.

In some embodiments, the at least one amplifier is configured to generate the at least one amplification signal for the at least one electrode based on a magnitude of a signal received at the at least one electrode. It may be desirable to generate the at least one amplification signal for the at least one electrode based on a magnitude of a signal received at the at least one electrode to modulate an amplification of the sensed signals only when required, which may result in power conservation. For example, the at least one amplifier may be configured to generate the at least one amplification signal for the at least one electrode when a magnitude of a signal received at the at least one electrode is less than X. In this example, the at least one amplifier may be configured to not generate the at least one amplification signal for the at least one electrode when a magnitude of a signal received at the at least one electrode is greater than X. By only magnifying the input signal when required, the amplifier in this example reduces power consumption of the system.

Disclosed embodiments include at least one multiplexer configured to multiplex at least two amplified signals based on the sensed electrical signals generated by the one or more neurons. A multiplexer may include any electronic circuit configured to receive signals from another circuit, such as an amplifier, and convert them into a single channel, using multiplexing techniques such as time-division multiplexing. In some embodiments, the sensing assembly is configured to multiplex a plurality of amplified signals to reduce the number of conductors exiting the sensing assembly. Using a multiplexer is desirable to sense electrical signals generated by the one or more neurons with substantially fewer wires or connectors than the number of input channels used to collect the electrical signals. As an example, a multiplexer may include a 32:1 analog multiplexer to multiplex input electrical signals into a single channel. In this example, the multiplexing ratio may be 32:1, by which 32 channels may be converted into a single channel. The multiplexed signals are then carried by the at least one signal lead toward a location outside of the brain.

Disclosed embodiments include at least one analog-to-digital converter configured to convert at least one amplified and multiplexed signal based on the sensed electrical signals generated by the one or more neurons to at least one digital signal. An analog-to-digital converter may include any electronic circuit configured to convert an analog signal, such as signals generated by neurons, into a digital signal. A variety of analog-to-digital converter architectures may be used with the disclosed embodiments. In one example, an analog-to-digital converter may be implemented as an integrated circuit. In this example, the analog-to-digital converter maybe configured as a metal-oxide semiconductor (MOS) mixed-signal integrated circuit chip that integrates both analog and digital circuits. In some embodiments, the integrated chip is configured to convert a plurality of multiplexed analog signals into digital signals to enable read-out of the data on a computer interface. A computer interface may include any processing device, including but not limited to a smartphone, a tablet, a smartwatch, a personal digital assistant, a desktop computer, a laptop computer, an IoT device, a dedicated terminal, and any other similar device.

In one embodiment, the neural probe with arrays of micro-electrodes for sensing, the amplifiers and the multiplexer are all created in a single integrated device using a complementary metal-oxide semiconductor (CMOS) process. In this embodiment, the signal lead may be connected to the neural probe device on one end, and to an application specific integrated circuit that will digitize multiplexed signals located within a processing unit externally on the other end. The entire integrated neural probe device, with the exception of the metal electrode sensors, may be encapsulated in a material to prevent moisture buildup in the device. In this embodiment, the probe and circuitry may be made in the same process, which reduces external noise and potential moisture issues that may be associated with a neural probe that is built by electrically bonding together a neural probe and the separately fabricated circuit component. It also reduces the overall form factor of the neural probe, by preventing the bonding of separate analogue and digital electronic parts and circuitry, which limits damage to the brain by insertion of the neural probe.

A location outside of the brain may include any area, locale, part, point, region, section, site, or any other position that is exterior to the brain, either entirely or partially. It may be desirable to carry the at least one multiplexed signal toward a location outside of the brain by the at least one signal lead to limit the amount and size of components that are introduced into the brain. As an example, the at least one multiplexed signal may be carried by the at least one signal lead toward a processing unit located on the skull, just below or on top of the skin. As another example, the at least one multiplexed signal may be carried by the at least one signal lead toward an external processor situated in the same room as the brain.

In some embodiments, the sensing assembly further comprises at least one filter configured to condition the sensed electrical signals or the at least one amplification signal. A filter configured to condition the sensed electrical signals or the at least one amplification signal may include device or process that removes some unwanted components or features from the sensed electrical signals or the at least one amplification signal. It may be desirable to configure a filter to condition the sensed electrical signals or the at least one amplification signal to reduce or smooth out high-frequency noise associated with a biological measurement, such as electrical signals measured from neurons. As one example, a low pass filter may be used to attenuate or minimize signal frequency components which are above a frequency band of interest and which are unrelated to electrical activity within the brain of a person. A potential frequency component unrelated to and not relevant to brain electrical activity may be a signal coupled from 50 Hz or 60 Hz AC power lines. In this example, a notch filter may be used to filter out these signals.

Figure 9:
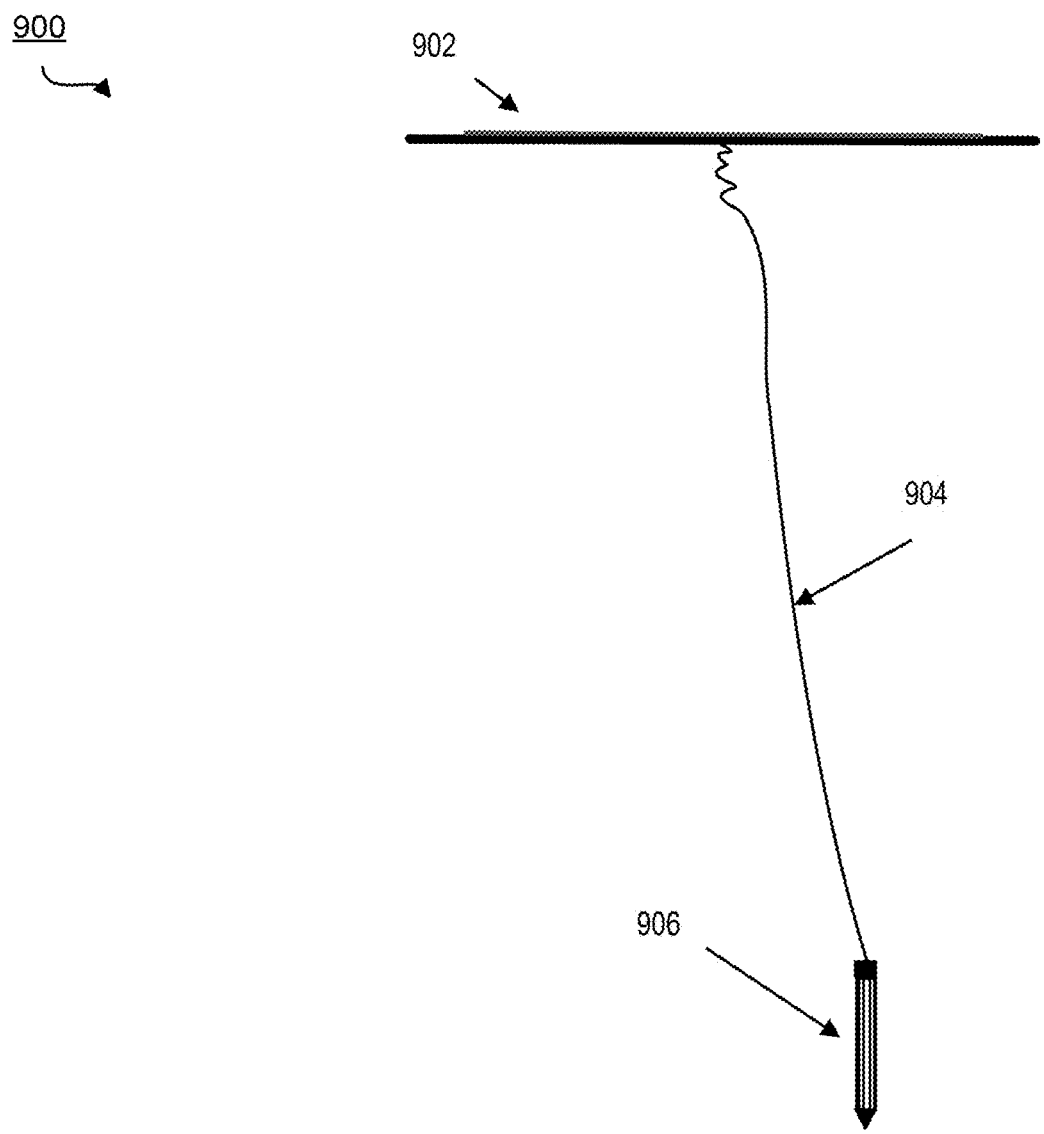
FIG. 9 illustrates an exemplary system for local amplification, multiplexing and analog-to-digital conversion of signals sensed from deep brain regions, consistent with some embodiments of the present disclosure.

FIG. 9 illustrates an exemplary system 900 for local amplification, multiplexing and analog-to-digital conversion of signals sensed from deep brain regions, consistent with some embodiments of the present disclosure. As shown in FIG. 9, the system 900 may include a processor unit 902 that includes a wireless data transmitter and power charger and furthermore contains an application specific integrated circuit or chip responsible for signal digitization, signal processing and stimulus generation. The processing unit 902 may be as small as 10 mm wide and 0.5 mm thick. The system 900 may include a signal lead 904 for data transmission of amplified and multiplexed analogue signals from inside the brain and for delivering stimulation pulses through the neural probe. The signal lead 904 may be approximately 8 cm long and less than 1 millimeter in diameter. The system 900 may include an integrated neural probe device 906 with dual-role micro-electrodes and integrated circuitry for local signal amplification and multiplexing of analogue signals. The system 900 may also be comprised of integrated electrodes, amplifiers and multiplexers fabricated as a single component with a CMOS process.

In some embodiments, the system further includes at least one processor configured to receive the at least one amplification signal and to cause transmission of one or more stimulation signals, in response. As used herein, "at least one processor" may constitute any physical device or group of devices having electric circuitry that performs a logic operation on an input or inputs. For example, the at least one processor may include one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by at least one processor may, for example, be pre-loaded into a memory integrated with or embedded into the controller or may be stored in a separate memory. The memory may include a Random Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively and may be co-located or located remotely from each other. The processors may be coupled electrically, magnetically, optically, acoustically, mechanically or by other means that permit them to interact. Transmission of one or more stimulation signals may include wired or wireless transmission.

It may be desirable to receive the at least one amplification signal and to cause transmission of one or more stimulation signals to provide stimulation signals based on feedback from the measured electrical signals from the one or more neurons, such that the overall system is a closed-loop feedback system. For example, the at least one amplification signal may indicate that the patient requires stimulation at a given intensity for one minute. In this example, providing the stimulation signal based on the sensed amplification signal may be desirable to optimize treatment based on feedback.

In some embodiments, the at least one processor is configured to identify one or more of the plurality of electrodes to receive a transmission of the one or more stimulation signals based on at least one detected characteristic of the at least one amplification signal. It may be desirable to receive a transmission of the one or more stimulation signals based on at least one detected characteristic of the at least one amplification signal to optimize stimulation to the relevant electrodes based on areas of the brain that require stimulation. As an example, the plurality of electrodes may include a first electrode extending into the hypothalamus and a second electrode extending into the thalamus. In this example, the amplification signal from the first electrode in the hypothalamus may indicate that stimulation is required at strength A and the amplification signal from the first electrode in the thalamus may indicate that stimulation is required at strength B. It would not be beneficial to stimulate at strength B in the hypothalamus or at strength A in the thalamus. Thus, the at least one processor may be configured to stimulate the first electrode extending into the hypothalamus with strength A and the second electrode extending into the thalamus with strength B.

Figure 10A:
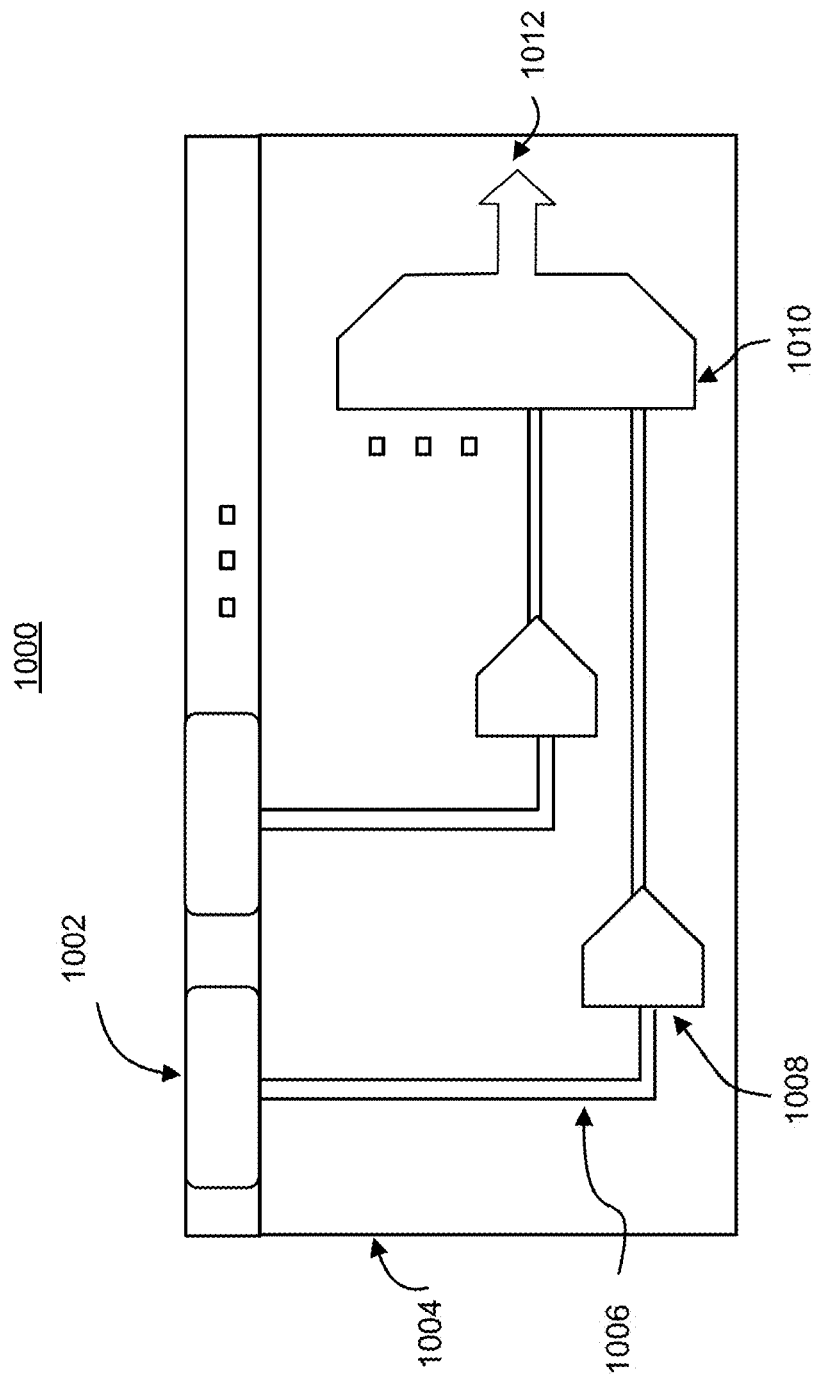
FIGS. 10A-10B illustrate various components of an exemplary system for local amplification, multiplexing and analog-to-digital conversion of signals sensed from deep brain regions, consistent with some embodiments of the present disclosure.
Figure 10B:
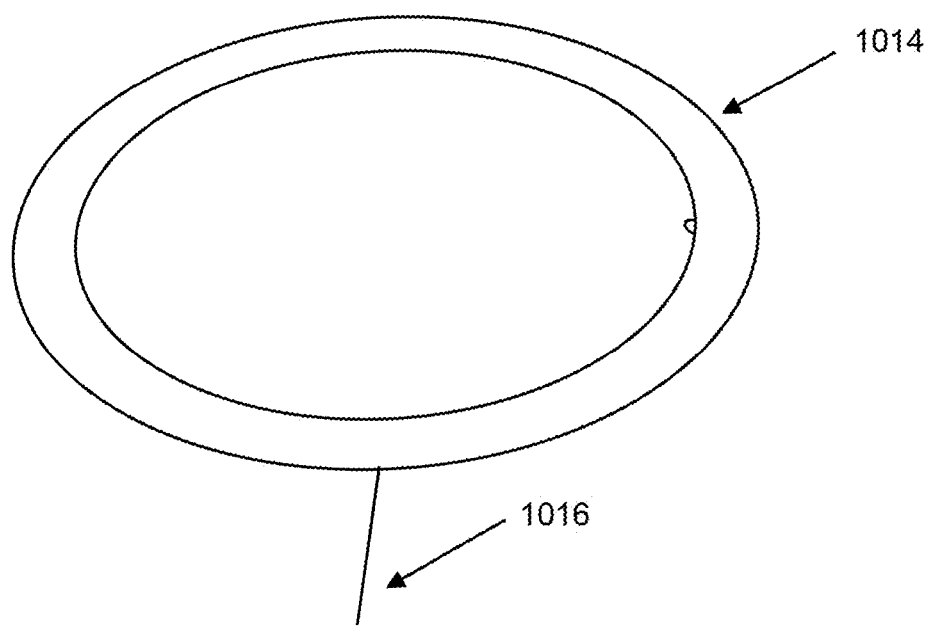

FIGS. 10A-10B illustrate various components of an exemplary system for local amplification and multiplexing of signals sensed from deep brain regions, consistent with some embodiments of the present disclosure. As shown in FIG. 10A, the neural probe system 1000 may include a probe with one or more micro-electrodes, such as electrode 1002. Electrode 1000 may be embedded with electronics, such as a dual-role electrode 1002 for recording or stimulating, a silicone probe shank 1004, an interconnect 1006 to internal CMOS circuitry, an analog signal amplifier 1008, an analog multiplexer circuit 1010, and a multiplexed analog output 1012. As shown in FIG. 10B, the system may include a processing unit 1014. Processing unit 1014 may be circular and may include a power source. Processing unit 1014 may be connected to a probe containing electrode assemblies such as electrode 1000 via signal lead 1016.

In some embodiments, the processing assembly 1014 is configured to be located on a skull of the brain and contains a chip for demultiplexing of analogue signals, analog-to-digital conversion, stimulus computing and stimulus generation and to transmit digital data via a wireless or wired connection. The processing assembly may include any component or combination of components configured to process input data and produce output data. It may be desirable to configure the processing assembly to be located on a skull of the brain to limit the number of system components inserted within the brain tissue.

In some embodiments, the system further includes a power assembly configured to be located on a skull of the brain and to provide power to the neural probe assembly located inside the brain. A power assembly may include a configuration of mechanical connections and conductive material arranged in such a way as to provide power or signal distribution to one or more components of the system, such as to stimulate neural tissue using the plurality of dual-role micro-electrodes. The power assembly may include a power source. Any power source can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and other similar devices. It may be desirable to configure the power assembly to be located on a skull of the brain to limit the number of system components inserted within the brain tissue. By locating the power assembly on the skull, the distance between the electrodes and the power assembly, and hence noise, is minimized while still avoiding placement of the power assembly within brain tissue. It may also be desirable to configure the power assembly outside of the brain for safety reasons and to avoid heat dissipation through brain tissue.

In some embodiments, the power assembly is configured to be charged via electrodynamic wireless power transmission, inductive power transmission, electromagnetic coupling, or resonant power coupling. Electrodynamic wireless power transmission may deliver electrical power from a transmitter coil to a compact electromechanical receiver over a range of distances using low-amplitude, low-frequency magnetic fields. An electrodynamic wireless power transfer system may use a receiver with a mechanically resonating or rotating permanent magnet. When subjected to a time-varying magnetic field, the mechanical motion of the resonating magnet may be converted into electricity by one or more electromechanical transduction schemes (e.g., electromagnetic/induction, piezoelectric, or capacitive). Compared to other wireless power transfer schemes, electrodynamic wireless power transfer systems leverage low-frequency magnetic fields (i.e., less than 1 kHz), which safely pass through conductive media and have higher human field exposure limits. Thus, it may be desirable to use electrodynamic wireless power transfer to wirelessly recharge biomedical devices, such as a neural probe. Inductive power transmission may involve power being transferred between coils of wire by a magnetic field. Inductive power transfer systems have many advantages towards wired solutions, such as the elimination of wires that can get tangled, the omission of open contacts and the simple overcoming of air gaps. Furthermore, wireless powering of implants in human brains, will allow patients to have more freedom of movement while powering their implants. Thus, inductive power transmission offers added value in applications such as powering a neural probe. Resonant power coupling may involve the use of coils capacitively loaded to form a tuned LC resonating at a common frequency, which allows for transmission of significant power over a wider range, which may be desirable for applications such as powering a neural probe.

Figure 11:
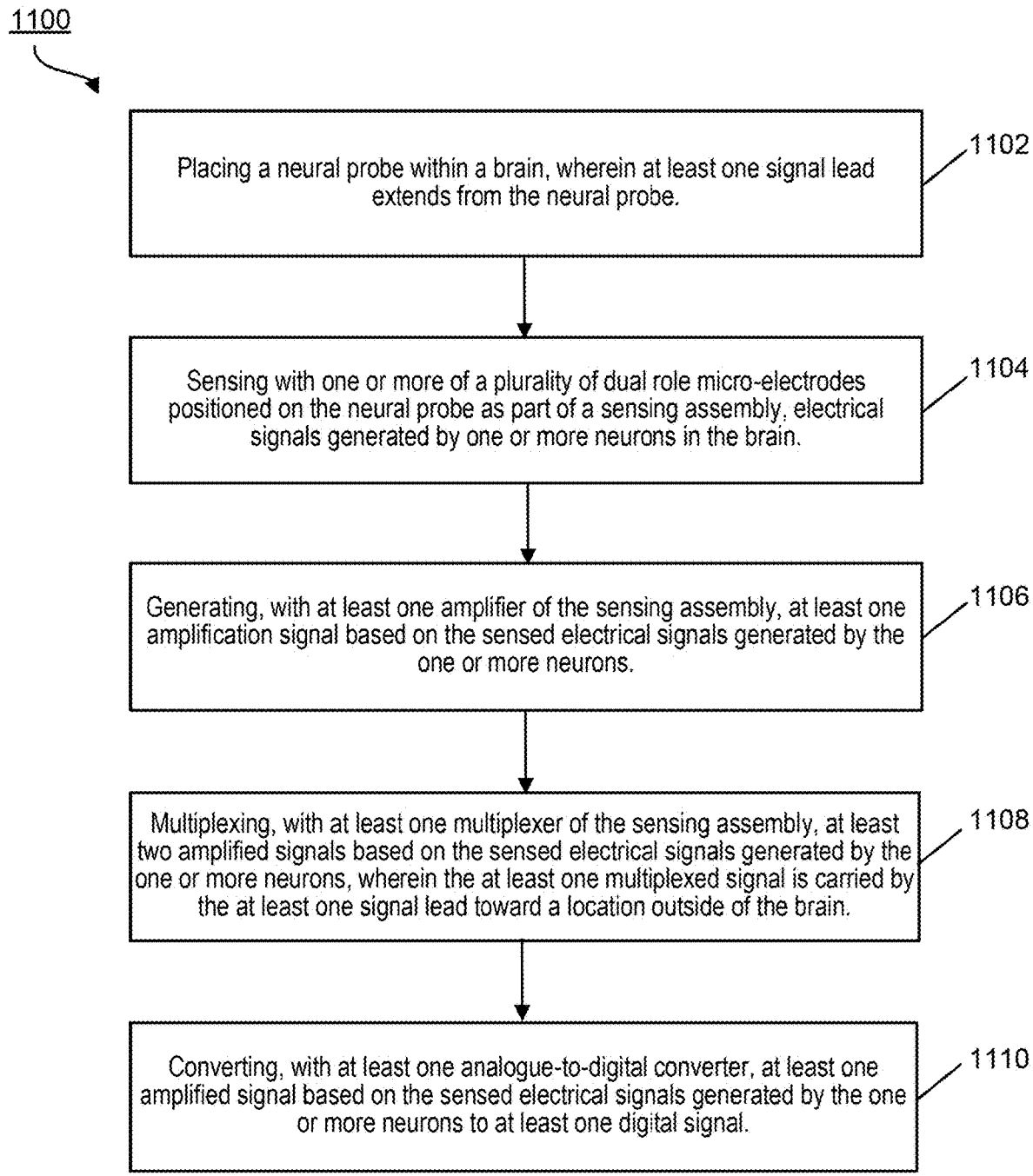
FIG. 11 illustrates a flowchart of a method for local amplification, multiplexing and analog-to-digital conversion of signals sensed from deep brain regions, and generation of a stimulus based on sensed signals consistent with some embodiments of the present disclosure.

FIG. 11 illustrates a flowchart 1100 of a method for local amplification and multiplexing and external analog-to-digital conversion of signals sensed from deep brain regions, consistent with some embodiments of the present disclosure. Method 1100 may include a step 1102 of placing a neural probe within a brain, wherein at least one signal lead extends from the neural probe. Method 1100 may include a step 1104 of sensing, with one or more of a plurality of dual role micro-electrodes positioned on the neural probe as part of a sensing assembly, electrical signals generated by one or more neurons in the brain. Method 1100 may include a step 1106 of generating, with at least one amplifier of the sensing assembly, at least one amplification signal based on the sensed electrical signals generated by the one or more neurons. Method 1100 may include a step 1108 of multiplexing, with at least one multiplexer of the sensing assembly, at least two amplified signals based on the sensed electrical signals generated by the one or more neurons, wherein the at least one multiplexed signal is carried by the at least one signal lead toward a location outside of the brain. Method 1100 may include a step 1110 of converting, with at least one analog-to-digital converter located within an external processing unit, at least one amplified signal based on the sensed electrical signals generated by the one or more neurons to at least one digital signal. An example of an external processing unit is processor unit 902, as shown in FIG. 9. A subsequent step may involve processing of signals with electronic circuitry within the external processing unit and determining whether delivery of stimulation through electrodes is required. A final step may include selecting electrodes for delivery of current stimulation and delivering the current, or voltage, to these selected electrodes, thereby closing the loop of sensing and stimulation.

While the present disclosure is described herein with reference to illustrative embodiments of systems and methods used for particular applications, such as for stimulation and sensing of deep brain regions including the basal ganglia, it should be understood that the embodiments described herein are not limited thereto. Those having ordinary skill in the art and access to the teachings provided herein will recognize additional modifications, applications, embodiments, and substitution of equivalents that all fall within the scope of the disclosed embodiments. Accordingly, the disclosed embodiments are not to be considered as limited by the foregoing or following descriptions.

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

Adaptive Closed-Loop DBS Stimulation Control Via Arrays of Micro-Electrodes

In the pursuit of improved devices for treating neurologic disorders of the central nervous system, and motor dysfunction in particular, the relationship between the electrical activity of neurons in the brain and corresponding behaviors is an area of interest. Also of interest is the effect of brain stimulation (e.g., deep brain stimulation) on neural activity and observed behaviors. The presently disclosed embodiments may include a neural interface comprising a plurality of micro-electrodes configured for placement in a deep region of the brain and for adaptive stimulation of neurons in the deep brain region based on observed neural activity or other biomarkers associated with the deep brain region. For example, pathological neural activity may occur in transient cycles, or may change in nature over time. Detecting such cycles or changes and responding to them in a closed loop feedback system may offer more consistent and effective therapeutic outcomes as compared to prolonged, non-adaptive stimulation of brain tissue. Pathological neural activity may be associated with the activity of single neurons or with the local field potentials associated with activity of groups and circuits of neurons.

Also considered by the present disclosure is the role of systems and apparatus in using dual-role micro-electrodes to locally sense single action potentials and local field potential activity, the characteristics of which may both serve as putative biomarkers in neurological disease states. For example, the activity of a single neurons may be analyzed with the utility of, for example, online and real-time spike sorting algorithms, which may be indicative of disease state and may be used to determine brain stimulation settings. In another example, the amplitudes and/or frequency components in local field potentials in a brain target area may be used to determine brain stimulation settings.

FIG. 12.A provides a diagrammatic cross-sectional view of components of a deep brain stimulation system in situ in accordance with embodiments of the present disclosure. For example, a neural probe 1214 may be used to stimulate deep brain tissue 1218 based on a sensed signal from local neurons or a group of neurons. Such responsive, adaptive stimulation may provide a therapeutic effect on disease symptoms in response to pathological brain activity.

With reference to FIGS. 12A to 14, the systems of the present disclosure include a neural probe 1214 for placement within a brain and a signal lead 1217 which may carry a sense signal from the neural probe 1214 to a processor assembly 1216 located outside of the brain. In response to the sense signal and one or more characteristics associated with the sense signal, the processor determines a target stimulation pattern and causes a signal generator to deliver a stimulation signal to the neural probe 1214 via the signal lead 1217. The sense signal may be a signal received by one or more electrodes associated with the neural probe or may include a signal derived from a signal received at the one or more electrodes. For example, the sense signal may be amplified, multiplexed, filtered, etc. prior to delivery to the processor.

Such closed-loop control may enable generation and delivery of a stimulation signal in response to a particular sense signal or pattern of sense signals received at the processing assembly. Further, the disclosed embodiments may also respond to changes or detected patterns in the received sense signal(s) by updating or altering the stimulation signals generated based on the received sense signals. For example, embodiments of the present disclosure system may be configured to automatically stimulate a desired brain region using a stimulation pattern generated in response to sensed neural activity patterns (or any other characteristics of received sense signals). Target stimulation patterns may also be determined in response to changes in measured parameters such as frequency bands or oscillations of neuronal activity. Such a determination may be based on changes in a measurable parameter relative to one or more predetermined thresholds. As one or more characteristics of the received sense signals may change over time, the processing assembly may adjust the target stimulation pattern to automatically adapt to observed changes in the received sense signals. In some cases, the disclosed systems may automatically change aspect(s) of a stimulation signal in response to one or more characteristics observed with respect to received sense signal(s). In other cases, however, the disclosed systems may also be configured to await clinician approval before implementing a target stimulation pattern determined based on observed sense signals.

Figure 12A:
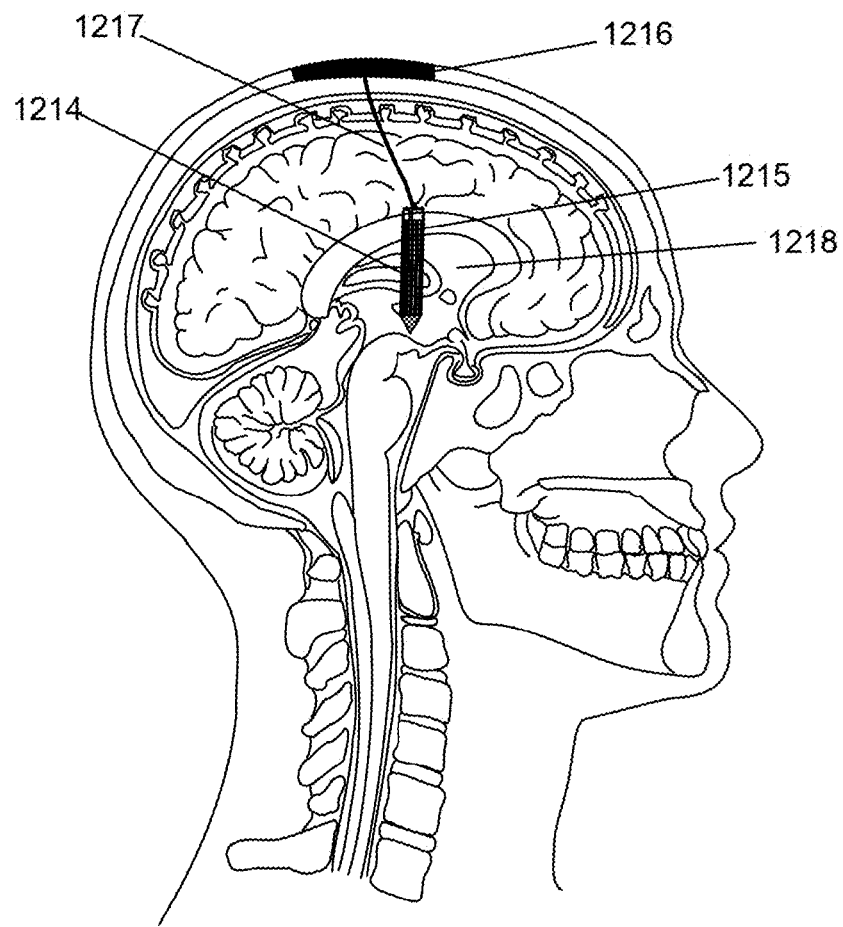
FIG. 12A illustrates a diagrammatic cross-sectional view of components of a deep brain stimulation system in situ in accordance with embodiments of the present disclosure.
Figure 12B:
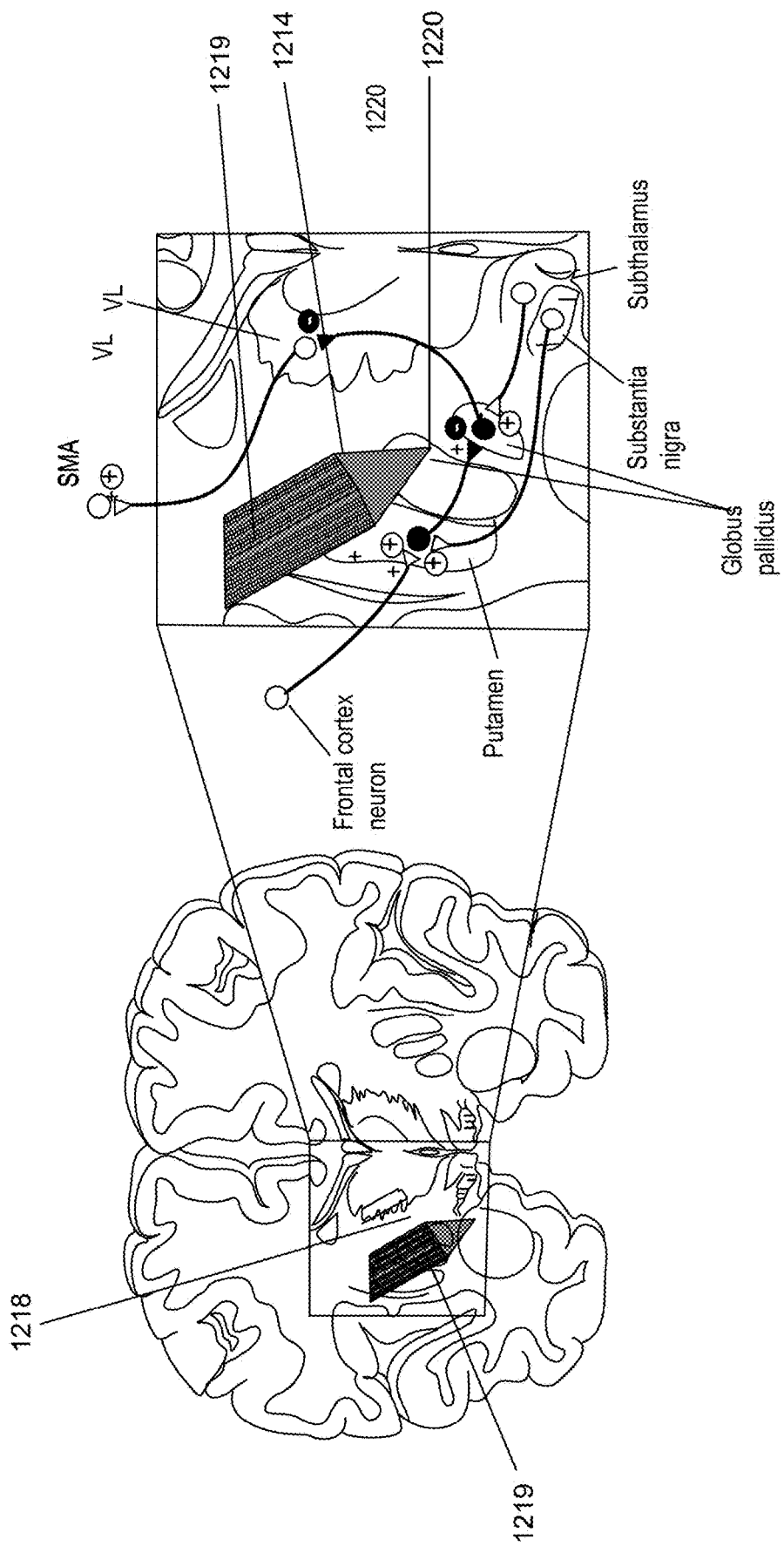
FIG. 12B illustrates a diagrammatic cross-sectional view of a neural probe of a deep brain stimulation system located in the basal ganglia of a brain in accordance with embodiments of the present disclosure.

Referring to FIGS. 12A and 12B, deep brain stimulation systems according to embodiments of the present disclosure may comprise at least:

- a neural probe with a plurality of dual role micro-electrodes 1214 configured for placement within a brain;
- at least one signal lead 1217 extending from the neural probe 1214;
- a sensing assembly with integrated electronic circuitry 1219 included on the neural probe 1214;
- at least one processing assembly 2016 external to the brain; and
- at least one stimulus generator embedded within the processing assembly 2016.

Devices and apparatus comprising these component parts may be suitable to form embodiments in accordance with the present disclosure. Sensing assembly 1215 may include at least one micro-electrode 1321 positioned on the neural probe 1214. In some cases, the at least one electrode 1321 may include a first group of electrodes dedicated to a sense function and a second group of electrodes dedicated to a stimulation function. In other cases, however, the at least one electrode 1321 can be configured for operation in either a sensing or a stimulation mode.

In a sensing mode, brain activity in the form of electrical signals generated by at least one neuron in the brain may interact with the at least one electrode 1321 to generate at least one sense signal. An interaction between the at least one sensing electrode 1321 and one or more electrical signals generated by at least one neuron in the brain may include, for example, the movement or generation of a charge in the at least one sensing electrode 1321 in response to one or more electrical signals generated by at least one neuron in the brain. Such electrical signals may comprise a change in the electrical activity or electrical potential of at least one neuron in the brain tissue 1218 surrounding the relevant sensing electrode 1321.

Sense signals are amplified and multiplexed on or near the sensing array 1215 on the neural probe 1214, and may be carried by the at least one signal lead 1217 to the at least one processing assembly 1216 where the sense signal will be converted in a digital signal and may be processed to extract, or otherwise determine, therefrom at least one characteristic of the at least one sense signal. The processing assembly may determine a target stimulation pattern based on the at least one characteristic of the at least one sense signal. Such a target stimulation pattern may be selected, for example, based on a library of target stimulation patterns available to the processing assembly. In some cases, the processing assembly 1216 may be associated with a system or device residing outside of the brain or cranial region of a patient. In some cases, the processing assembly 1216 may house a stimulus generator 1218 and a power source 1222.

Various observed/sensed characteristics of received sense signals may be used as a basis for determining appropriate stimulation signals and stimulation patterns to be delivered via electrodes 1321. For example, the at least one characteristic of the at least one sense signal may comprise one or more of a frequency, waveform, amplitude, pulse duration, noise level, polarity, amplitude trending direction and/or rate, etc. Such characteristics of the at least one sense signal may also include patterns observed over time relative to received sense signals. Stimulation signals may be generated based on observed variations over time of at least one of a frequency, waveform, amplitude, pulse duration, noise level, polarity, etc. associated with the at least one sense signal. Indeed, in some circumstances a new or altered target stimulation pattern may be determined in response to a variation in at least one sense signal over time. For example, a new or altered target stimulation pattern may be determined in response to a change in at least one characteristic of the at least one sense signal from normal to pathological over a period of measurement. In this way, various electrical signals of at least one neuron or a group of neurons in the brain may be measured and/or quantified by the at least one processor to determine a suitable stimulation response.

Further, characteristics of the at least one sense signal used to determine stimulation responses may include an identification of a particular electrode 1321 from which at least one sense signal originated. Such an identification may enable a determination of a region of brain tissue 1218 associated with a received sense signal. Thereby, it may be determined by the processing assembly which particular electrode 1321 is the source of the sense signal and, in turn, which electrode(s) should be involved in delivering desired stimulation signal(s) or signal pattern.

The external processor assembly may comprise at least one unitary processor and/or at least one network of processors communicatively coupled in a network such that they may coordinate the processing of data as described above in relation to data processing.

The at least one neural probe may comprise at least one integrated circuits (IC) such as an application-specific integrated circuit (ASIC) and/or a field-programmable gate array (FPGA). Such integrated circuits may comprise at least one metal-oxide-semiconductor field-effect transistor (MOSFET) such as a complementary metal-oxide-semiconductor (CMOS). The at least one neural interface may also comprise a processing unit as part of a computer.

In embodiments in which the at least one processor comprises more than one processor, the several processors may be different or the same and/or maybe configured for the same or different processing.

According to embodiments of the present disclosure, the at least one processing assembly may be further configured to determine the target stimulation pattern based on an observed change in the at least one characteristic of the at least one sense signal. Thereby, a target stimulation pattern may be determined in response to a detected pathological sense signal and therefore the electrical activity of the relevant brain tissue 1218 may be returned to normal and thereby the symptoms of the pathology may be treated.

Furthermore, the at least one processor may be further configured to cause the stimulus generator to deliver the one or more stimulation signals after receiving an input indicating user approval. Thereby, the delivery of the one or more stimulation signals may be overseen by a user. For example, such a user may be a physician or some otherwise qualified medical practitioner with authority, for example, to confirm that the determined target stimulation pattern is likely to provide a therapeutic benefit.

In some embodiments of the present disclosure, the at least one processing assembly may be configured to adjust one or more aspects of the target stimulation pattern based on received user input. The user may thereby contribute to the effective functioning of the systems of the present disclosure by, for example, providing an input that prompts the at least one processor to adjust one or more aspects of the target stimulation pattern to improve the therapeutic efficacy of the target stimulation pattern and/or avoid a technical malfunctioning of the system.

The signal generator may deliver one or more stimulation signals to the at least one electrode 1321 (e.g., a set of electrodes 1321 configured to operate in a stimulation mode) via the at least one signal lead 1217. The stimulation signals may be selectively provided to electrodes within a set of dual-role electrodes to activate the set of stimulation electrodes according to the target stimulation pattern. In some cases, a single conductor associated with the signal lead 1217 may carry both the sense signal(s) and the generated stimulation signal(s). In other cases, however, different conductors included in lead 1217 may be used to carry the sense and stimulation signals. Using such a feedback-based stimulation approach, activity of brain tissue 1218 in a vicinity of the neural probe 1214 may be sensed, and the brain may be responsively treated therapeutically, via local electrical stimulation.

The at least one signal lead 1217 may comprise a cable suitable for data and/or power transmission and may extend from the neural probe 1214 located within a brain to the surface of the skull. In circumstances in which the neural probe 1214 is located in the deep brain, for example, the cable may have a length of approximately 4 cm or more. The at least one signal lead 1217 may have a length of at least 60 mm or at least 80 mm, for example. One or more cables associated with signal lead 1217 may have a diameter less than 1 mm, which may be desirable to reduce the disruption to the brain tissue through which the cable may pass while providing sufficient volume to allow the transmission of data and/or power as described elsewhere herein. As shown in FIG. 13B, the neural probe may also comprise a pointed tip 1220 for penetrating neural tissue while reducing damage to brain tissue. In another example, the neural probe may have a blunted tip. The at least one signal lead 1217 extends from the neural probe 1214 and is utilized by the at least one processing assembly to receive at least one sense signal and deliver one or more stimulation signals produced by a stimulus generator. As described above, the signal lead 1217 may extend from the neural probe 1214 within a brain to the surface of the skull. In some cases, lead 1217 may include multiple conductors. For example, in some cases, one or more conductors may be included for each of the available electrodes 1321.

The stimulus generator may comprise a power source such as a battery and stimulation generation circuitry configured to produce stimulation signals such as impulses or waveforms with a certain amplitude and frequency. The produced stimulation signals, when transmitted to electrode(s) 1321, may stimulate brain tissue 1218 according to a predetermined stimulation pattern.

In some embodiments, the at least one processing assembly may be located outside of the brain but still within or on the person within who the neural probe 1214 is located. In such embodiments, the at least one processor may be located on a surface interface 1216 of the deep brain stimulation system located for example on the skull of the person. Other locations for the at least one processing assembly on the person may include: on the shoulder, behind the ear or otherwise attached to the body. In some embodiments of the present disclosure, the at least one processor may be located away from the person. In such embodiments, the transmission of the sense signal and/or the stimulation signal between the neural probe 1214 and the at least one processor may occur via wireless transmission.

In some cases, signal amplification and multiplication, among other functions, may be implemented by integrated circuitry associated with the neural probe. And data processing functions and stimulus generation may be performed by one or more processing devices located outside of the brain.

Electrodes 1321 of the present disclosure may include dedicated stimulating electrodes, dedicated sensing electrodes, and/or dual role micro-electrodes configured to operate in both sensing and stimulating modes positioned on neural probe 1214. The electrodes may be arranged in various patterns (e.g., rectangular arrays, hexagonal arrays, etc.). Some or all of the electrodes may have a similar size and shape. Alternatively, at least some of the electrodes may be of various sizes and shapes.

In embodiments that include dedicated sensing electrodes and dedicated stimulating electrodes, such electrodes may be arranged in any suitable pattern. For example, in some cases, the sensing electrodes may be arranged in a first group displaced from a second group including the stimulation electrodes. In other cases, a group of sensing electrodes may at least partially overlap with a group of stimulation electrodes. In still other cases, a set of stimulation electrodes may be spatially distributed among a set of sensing electrodes. In any case, stimulation electrodes may be selectively activated according to any desired target stimulation pattern to generate a customized stimulation pattern and customized electrical field sizes and shapes within brain tissue (e.g., customized based on observed characteristics of one or more received sense signals).

Some or each of the micro-electrodes 1321 of the neural probe 1214 (FIGS. 12B and 13B) may interface with neural tissue and sense flow of ionic currents generated by at least one neuron in the brain to generate a sense signal. Such electrodes among electrodes 1321 may be referred to as sensing electrodes. As described above, one or more of the sensing electrodes among electrodes 1321 may also be configured to serve as a stimulation electrode. Similarly, any of the electrodes 1321 may be configured to function solely as a stimulation electrode. Using such an arrangement of electrodes 1321 on neural probe 1214, local electrical field potentials and/or action potentials associated with surrounding brain tissue 1218 may be detected. In turn and based on one or more sensed characteristics associated with these sensed neural activity signals, stimulation signals with certain characteristics in terms of amplitude, timing and frequency may be designed and delivered to various regions of brain tissue 1218. The brain regions to which stimulation signals are delivered may depend on a particular pattern of electrodes 1321 activated on neural probe 1214.

One or more sensing electrodes among electrodes 1321 may be configured to sense electrical signals from neurons within a 200-micron radius from an area of the neural probe 1214 on which the at least one sensing electrode is located. For example, in such a configuration, a sensing electrode may be sensitive enough to detect electrical changes in brain tissue 1218 up to 200 microns from a surface of the electrode. Such a configuration of a sensing electrode may include metals such as platinum, platinum iridium, iridium oxide, or titanium nitride.

To selectively stimulate brain tissue 1218 in response to received sense signals, at least one processing assembly may determine suitable characteristics of a stimulation signal to deliver to a set of stimulation electrodes among electrodes 1321. Such characteristics of the stimulation signal(s) may include a magnitude, duration, frequency, polarity, duty cycle, etc. associated with one or more stimulation pulses to be delivered to selected electrodes. The pattern of electrodes receiving stimulation signals may also be determined by the at least one processing assembly. In some cases, all available electrodes may receive a stimulation signal. In other cases, only a subset of available stimulation electrodes receives stimulation signals, and the subset of stimulation electrodes may be selected according to a desired stimulation pattern to provide relative to brain tissue 1218. For example, the subset of stimulating electrodes may be selectively activating in a checkerboard pattern; a circular, square, or rectangular pattern; etc. The one or more stimulation signals that may be generated by the signal generator and delivered to a set of stimulation electrodes 1321 may be sufficient to stimulate or excite the brain tissue 1218 within the proximity of the set of stimulation electrodes 1321. The at least one processing assembly may include one or more signal generators to produce the desired stimulation signals to be delivered to selected electrodes 1321 via lead 1217.

Different stimulation signals may be delivered to different dual-role micro-electrodes used for stimulating. A first stimulation signal, for example, may be delivered to a first electrode and may differ in at least one respect from a second stimulation signal delivered to a second electrode within the set of dual-role micro-electrodes. Differences among stimulation signals provided to different dual role micro-electrodes may include variations in signal amplitude, phase, duration, frequency, duty cycle, polarity, etc.

The parameters of the stimulation signals may be selected based on the frequency components embedded in the sensed local field potential on at least one of the dual role micro-electrodes. In one example, if an increase, or a decrease in the beta frequency band is detected, a stimulus pattern may be triggered to be delivered to a set of nearby dual role electrodes. Such a stimulation pattern will involve biphasic, charge balanced pulses of less than 100 microseconds in duration and delivered at regular intervals resulting in a frequency of at least 100 Hz. In other examples, changes in gamma, delta, or alpha frequencies may trigger such a stimulus pattern to be delivered through the one or more electrodes selected for stimulation. In other embodiments, sensed signals may include specific patterns of action potential firing that will be used to trigger stimulation. Action potential rates may increase, or decrease below certain thresholds, which may trigger the delivery of a stimulus pattern to selected electrodes. Action potential firing may also become more or less regular, or variable, or in other ways change their dynamics, which may be reflective of disease symptoms, and could be used to trigger stimulation patterns. In addition to typical and regular stimulation frequencies of at least 100 Hz delivered in a continuous fashion, stimulation patterns may involve biphasic stimuli that are delivered at frequencies below 100 Hz, or at irregular intervals and/or for discontinuous time periods.

FIG. 14 provides a flowchart of an exemplary method associated with the presently disclosed embodiments. At step 1402, a sense signal is received. In response, at steps 1403 and 1404, a processing assembly determines an appropriate stimulation signal/stimulation signal pattern in response to the received sense signal. In some cases, at step 1407, the processor causes one or more signal generators to deliver stimulation signals according to the target signal and pattern developed in response to the received sense signals. In other cases, delivery of the stimulation signals may be conditioned upon an optional step 1405 of receiving user approval for the generated signal(s)/patterns (e.g., clinician approval). Further, in some cases, delivery of the stimulation signals may proceed after one or more aspects of the target stimulation signal(s)/pattern are optionally adjusted based on user input received at step 1406.

Also disclosed herein are following clauses.

Clause 1. A neural interface, comprising:
a neural probe configured for placement within a brain;
at least one signal lead extending from the neural probe; and
a sensing assembly included on the neural probe, where the sensing assembly includes:
a plurality of dual-role electrodes positioned on the neural probe, wherein each of the dual-role electrodes is configured to sense electrical signals generated by one or more neurons in the brain and to convey to the at least one signal lead one or more sense signals generated based on the sensed electrical signals, and wherein each of the dual-role electrodes is configured to receive, via the at least one signal lead, a stimulation signal selectively delivered from a stimulus generator.

Clause 2. The neural interface of the preceding clause, wherein the at least one neural probe includes a plurality of conductors, such that each of the plurality of dual-role electrodes is associated with a single conductor configured to both carry sensed signals from and to deliver a stimulation signal to one of the plurality of dual-role electrodes.

Clause 3. The neural interface of any of the preceding clauses, wherein the at least one signal lead includes a plurality of conductors, such that each of the plurality of dual-role electrodes is associated with at least two conductors, wherein a first of the at least two conductors is configured to carry sensed signals from a particular one of the plurality of dual-role electrodes, and a second of the at least two conductors, different from the first of the at least two conductors, is configured to deliver a stimulation signal to the particular one of the plurality of dual-role electrodes.

Clause 4. The neural interface of any of the preceding clauses, wherein stimulation signals selectively delivered from the signal generator to corresponding ones of the plurality of electrodes cause activation of at least some of the plurality of electrodes according to a selected stimulation pattern.

Clause 5. The neural interface of any of the preceding clauses, wherein stimulation signals selectively delivered from the signal generator to corresponding ones of the plurality of electrodes cause activation during a first time period of a first set of the plurality of electrodes to provide a first stimulation pattern and cause activation, during a second time period different from the first time period, of a second set of the plurality of electrodes to provide a second stimulation pattern.

Clause 6. The neural interface of any of the preceding clauses, wherein each of the plurality of electrodes comprises at least one conductor.

Clause 7. The neural interface of any of the preceding clauses, wherein the at least one conductor includes a surface comprising a surface area between 25 and 400 square microns.

Clause 8. The neural interface of any of the preceding clauses, wherein the at least one conductor comprises gold, titanium nitrate or platinum iridium.

Clause 9. The neural interface of any of the preceding clauses, wherein each of the plurality of electrodes has an impedance of between 1 kOhms and 1 MOhm.

Clause 10. The neural interface of any of the preceding clauses, wherein the sensing assembly comprises circuitry operable to switch each of the plurality of electrodes between a sensing mode and a stimulation mode.

Clause 11. The neural interface of any of the preceding clauses, wherein the plurality of electrodes is arranged in at least one array.

Clause 12. The neural interface of any of the preceding clauses, wherein the neural probe comprises at least one facet on which at least some of the plurality of electrodes are disposed.

Clause 13. The neural interface of any of the preceding clauses, wherein the neural probe comprises two facets, including a first facet and a second facet on opposing faces of the neural probe, on which at least some of the plurality of electrodes are disposed.

Clause 14. The neural interface of any of the preceding clauses, wherein the neural probe comprises three facets on which at least some of the plurality of electrodes are disposed.

Clause 15. The neural interface of any of the preceding clauses, wherein the neural probe comprises four facets on which at least some of the plurality of electrodes are disposed.

Clause 16. The neural interface of any of the preceding clauses, wherein the neural probe is non-centric.

Clause 17. The neural interface of any of the preceding clauses, wherein the one or more sense signals are amplified by an amplifier local to the neural probe.

Clause 18. The neural interface of any of the preceding clauses, wherein in response to a delivered stimulation signal, each of the plurality of electrodes is configured to cause emission of an electrical field extending into the brain by at least 50 microns.

Clause 19. The neural interface of any of the preceding clauses, wherein each of the plurality of electrodes is configured to sense electrical signals generated by brain neurons located within a range of up to 200 microns.

Clause 20. The neural interface of any of the preceding clauses, further comprising a power assembly configured to be located on the skull of the brain that can be charged via electrodynamic wireless power transmission, inductive power transmission, or resonant power coupling.

Clause 21. A system for local amplification, multiplexing and analog-to-digital conversion of signals sensed from deep brain regions, comprising:
  a neural probe configured for placement within a brain;
  at least one signal lead extending from the neural probe; and
  a sensing assembly included on the neural probe, where the sensing assembly includes:
  a plurality of electrodes positioned on the neural probe, wherein one or more of the plurality of electrodes are configured to sense electrical signals generated by one or more neurons in the brain;
  at least one amplifier configured to generate at least one amplification signal based on the sensed electrical signals generated by the one or more neurons; and
  at least one multiplexer configured to multiplex at least two amplified signals based on the sensed electrical signals generated by the one or more neurons
  an externally located processing assembly with electrical components for analogue to digital conversion of signals, a signal generator, a power source, and electronic circuitry enabling wireless transfer of data and wireless charging of power.

Clause 22. The system of the preceding clause, wherein one or more of the plurality of electrodes are configured to stimulate one or more neurons in the brain.

Clause 23. The system of any of the preceding clauses, wherein the plurality of electrodes includes one or more dual-role electrodes selectively configurable to stimulate one or more neurons in the brain or to sense electrical signals generated by one or more neurons in the brain.

Clause 24. The system of any of the preceding clauses, wherein the system further includes at least one processor, located outside the brain, configured to receive the at least one amplification signal and to cause transmission of one or more stimulation signals.

Clause 25. The system of any of the preceding clauses, wherein the at least one external processor is configured to identify one or more of the plurality of electrodes to receive a transmission of the one or more stimulation signals based on at least one detected characteristic of the at least one amplification signal.

Clause 26. The system of any of the preceding clauses, wherein the at least one signal lead includes one or more electrical conductors.

Clause 27. The system of any of the preceding clauses, wherein the at least one signal lead has a length of at least 40 millimeters.

Clause 28. The system of any of the preceding clauses, wherein the at least one signal lead has a length of at least 50 millimeters.

Clause 29. The system of any of the preceding clauses, wherein the at least one signal lead has a length of at least 60 millimeters.

Clause 30. The system of any of the preceding clauses, wherein the at least one signal lead has a length of at least 70 millimeters.

Clause 31. The system of any of the preceding clauses, wherein the at least one signal lead has a length of at least 80 millimeters.

Clause 32. The system of any of the preceding clauses, wherein the at least one amplifier includes at least one of a low-noise operational transconductance amplifier, a Miller operational transconductance amplifier, a current mirror operational transconductance amplifier, or a differential self-biased operational transconductance amplifier.

Clause 33. The system of any of the preceding clauses, wherein the one or more of the plurality of electrodes are configured to sense electrical signals from individual neurons, or a plurality of neurons within a 200-micron radius from an area of the neural probe on which the one or more of the plurality of electrodes are located.

Clause 34. The system of any of the preceding clauses, wherein the at least one amplifier is configured to vary a gain associated with the at least one amplification signal based on at least one characteristic of the sensed electrical signals.

Clause 35. The system of any of the preceding clauses, wherein the at least one amplifier is configured to generate the at least one amplification signal for the at least one electrode based on a magnitude of a signal received at the at least one electrode.

Clause 36. The system of any of the preceding clauses, wherein the at least one amplifier is configured to generate the at least one amplification signal for the at least one electrode based on a position of the at least one electrode on the neural probe.

Clause 37. The system of any of the preceding clauses, wherein the sensing assembly further comprises at least one filter configured to condition the sensed electrical signals or the at least one amplification signal.

Clause 38. The system of any of the preceding clauses, wherein the sensing assembly is configured to multiplex a plurality of amplified signals to reduce the number of conductors exiting the sensing assembly.

Clause 39. The system of any of the preceding clauses, wherein the external processing assembly is configured to convert a plurality of analog signals into digital signals to enable read-out of the data on a computer interface.

Clause 40. The system of any of the preceding clauses, wherein the neural probe and associated circuitry are part of an integrated device created using a complementary metal-oxide semiconductor (CMOS) fabrication process.

Clause 41. The system of any of the preceding clauses, further comprising a data processing assembly configured to be located on a skull of the brain and to transmit digital data via a wireless or wired connection.

Clause 42. The system of any of the preceding clauses, further comprising a power assembly configured to be located on a skull of the brain and to provide power to the sensing assembly located inside the brain.

Clause 43. The system of any of the preceding clauses, wherein the power assembly is configured to be charged via electrodynamic wireless power transmission, inductive power transmission, or resonant power coupling.

Clause 44. A deep brain stimulation system, comprising:
  a neural probe configured for placement within a brain;
  at least one signal lead extending from the neural probe;
  a sensing assembly included on the neural probe, where the sensing assembly includes at least one sensing micro-electrode positioned on the neural probe and at least one stimulation electrode positioned on the neural probe; and
  at least one processor assembly configured to:
  receive, via the at least one signal lead, at least one sense signal generated in response to interaction between the at least one sensing electrode and one or more electrical signals generated by at least one neuron in the brain;

deliver at least one of a library of preset target stimulation patterns;
determine a target stimulation pattern based on at least one characteristic of the at least one sense signal; and
cause a signal generator to deliver, via the at least one signal lead, one or more stimulation signals to a set of stimulation electrodes among the at least one stimulating electrode to activate the set of stimulation electrodes according to the target stimulation pattern.

Clause 45. The deep brain stimulation system of the preceding clause, wherein the set of stimulation electrodes includes at least one of the plurality of dual-role microelectrodes.

Clause 46. The deep brain stimulation system of any of the preceding clauses, wherein the set of stimulation electrodes includes two or more of the dual-role micro-electrodes.

Clause 47. The deep brain stimulation system of any of the preceding clauses, wherein the set of dual-role electrodes is spatially distributed relative to the neural probe and wherein the set of stimulation electrodes is selected based on the target stimulation location.

Clause 48. The deep brain stimulation system of any of the preceding clauses, wherein the at least one sensing electrode is configured to serve also as a stimulation electrode.

Clause 49. The deep brain stimulation system of any of the preceding clauses, wherein the at least one stimulating electrode is configured to serve also as sensing electrode.

Clause 50. The deep brain stimulation system of any of the preceding clauses, wherein a first stimulation signal delivered to a first stimulation electrode within the set of stimulation electrodes differs in at least one respect from a second stimulation signal delivered to a second stimulation electrode within the set of stimulation electrodes.

Clause 51. The deep brain stimulation system of any of the preceding clauses, wherein the at least one signal lead has a length of at least 40 mm.

Clause 52. The deep brain stimulation system of any of the preceding clauses, wherein the at least one signal lead has a length of at least 70 mm.

Clause 53. The deep brain stimulation system of any of the preceding clauses, wherein the at least one characteristic of the at least one sense signal comprises one or more of a frequency, waveform, amplitude, or integration of a waveform associated with the at least one sense signal.

Clause 54. The deep brain stimulation system of any of the preceding clauses, wherein the at least one characteristic of the at least one sense signal comprises an identification of a particular electrode from which the at least one sense signal originated.

Clause 55. The deep brain stimulation system of any of the preceding clauses, wherein the at least one characteristic of the at least one sense signal comprises a location of an electrode from which the at least one sense signal originated.

Clause 56. The deep brain stimulation system of any of the preceding clauses, wherein the at least one characteristic of the at least one sense signal comprises a variation in time of at least one of a frequency, waveform, amplitude, or integration of a waveform associated with the at least one sense signal.

Clause 57. The deep brain stimulation system of any of the preceding clauses, wherein the at least one sensing electrode is configured to sense electrical signals from neurons within a 200-micron radius from an area of the neural probe on which the at least one sensing electrode is located.

Clause 58. The deep brain stimulation system of any of the preceding clauses, wherein the at least one processor is further configured to determine the target stimulation pattern based on an observed change in the at least one characteristic of the at least one sense signal.

Clause 59. The deep brain stimulation system of any of the preceding clauses, wherein the at least one processor is further configured to cause the signal generator to deliver the one or more stimulation signals after receiving an input indicating user approval.

Clause 60. The deep brain stimulation system of any of the preceding clauses, wherein the at least one processor is configured to adjust one or more aspects of the target stimulation pattern based on received user input.

Disclosed embodiments may include any one of the following bullet-pointed features alone or in combination with one or more other bullet-pointed features, whether implemented as a system, device, and/or method.

- a neural interface
- a neural probe configured for placement within a brain
- at least one signal lead extending from the neural probe
- a sensing assembly included on the neural probe
- a plurality of dual-role electrodes positioned on the neural probe
- each of the dual-role electrodes is configured to sense electrical signals generated by one or more neurons in the brain and to convey to the at least one signal lead one or more sense signals generated based on the sensed electrical signals
- each of the dual-role electrodes is configured to receive, via the at least one signal lead, a stimulation signal selectively delivered from a stimulus generator.
- the at least one neural probe includes a plurality of conductors
- each of the plurality of dual-role electrodes is associated with a single conductor configured to both carry sensed signals from and to deliver a stimulation signal to one of the plurality of dual-role electrodes
- the at least one signal lead includes a plurality of conductors
- each of the plurality of dual-role electrodes is associated with at least two conductors
- a first of the at least two conductors is configured to carry sensed signals from a particular one of the plurality of dual-role electrodes
- a second of the at least two conductors, different from the first of the at least two conductors, is configured to deliver a stimulation signal to the particular one of the plurality of dual-role electrodes
- stimulation signals selectively delivered from the signal generator to corresponding ones of the plurality of electrodes cause activation of at least some of the plurality of electrodes according to a selected stimulation pattern
- stimulation signals selectively delivered from the signal generator to corresponding ones of the plurality of electrodes cause activation during a first time period of a first set of the plurality of electrodes to provide a first stimulation pattern and cause activation, during a second time period different from the first time period, of a second set of the plurality of electrodes to provide a second stimulation pattern
- each of the plurality of electrodes comprises at least one conductor
- the at least one conductor includes a surface comprising a surface area between 25 and 400 square microns the at least one conductor comprises gold, titanium nitrate or platinum iridium each of the plurality of electrodes has an impedance of between 1 kOhms and 1 MOhm the sensing assembly comprises circuitry operable to switch each of the plurality of electrodes between a sensing mode and a stimulation mode the plurality of electrodes is arranged in at least one array the neural probe comprises at least one facet on which at least some of the plurality of electrodes are disposed the neural probe comprises two facets, including a first facet and a second facet on opposing faces of the neural probe, on which at least some of the plurality of electrodes are disposed the neural probe comprises three facets on which at least some of the plurality of electrodes are disposed the neural probe comprises four facets on which at least some of the plurality of electrodes are disposed the neural probe is non-centric the one or more sense signals are amplified by an amplifier local to the neural probe in response to a delivered stimulation signal, each of the plurality of electrodes is configured to cause emission of an electrical field extending into the brain by at least 50 microns each of the plurality of electrodes is configured to sense electrical signals generated by brain neurons located within a range of up to 200 microns a power assembly configured to be located on the skull of the brain that can be charged via electrodynamic wireless power transmission, inductive power transmission, or resonant power coupling a system for local amplification, multiplexing and analog-to-digital conversion of signals sensed from deep brain regions a neural probe configured for placement within a brain at least one signal lead extending from the neural probe a sensing assembly included on the neural probe a plurality of electrodes positioned on the neural probe one or more of the plurality of electrodes are configured to sense electrical signals generated by one or more neurons in the brain at least one amplifier configured to generate at least one amplification signal based on the sensed electrical signals generated by the one or more neurons at least one multiplexer configured to multiplex at least two amplified signals based on the sensed electrical signals generated by the one or more neurons an externally located processing assembly with electrical components for analogue to digital conversion of signals a signal generator a power source electronic circuitry enabling wireless transfer of data and wireless charging of power one or more of the plurality of electrodes are configured to stimulate one or more neurons in the brain the plurality of electrodes includes one or more dual-role electrodes selectively configurable to stimulate one or more neurons in the brain or to sense electrical signals generated by one or more neurons in the brain at least one processor, located outside the brain, configured to receive the at least one amplification signal and to cause transmission of one or more stimulation signals the at least one external processor is configured to identify one or more of the plurality of electrodes to receive a transmission of the one or more stimulation signals based on at least one detected characteristic of the at least one amplification signal the at least one signal lead includes one or more electrical conductors the at least one signal lead has a length of at least 40 millimeters the at least one signal lead has a length of at least 50 millimeters the at least one signal lead has a length of at least 60 millimeters the at least one signal lead has a length of at least 70 millimeters the at least one signal lead has a length of at least 80 millimeters the at least one amplifier includes at least one of a low-noise operational transconductance amplifier, a Miller operational transconductance amplifier, a current mirror operational transconductance amplifier, or a differential self-biased operational transconductance amplifier the one or more of the plurality of electrodes are configured to sense electrical signals from individual neurons, or a plurality of neurons within a 200-micron radius from an area of the neural probe on which the one or more of the plurality of electrodes are located the at least one amplifier is configured to vary a gain associated with the at least one amplification signal based on at least one characteristic of the sensed electrical signals the at least one amplifier is configured to generate the at least one amplification signal for the at least one electrode based on a magnitude of a signal received at the at least one electrode the at least one amplifier is configured to generate the at least one amplification signal for the at least one electrode based on a position of the at least one electrode on the neural probe the sensing assembly further comprises at least one filter configured to condition the sensed electrical signals or the at least one amplification signal the sensing assembly is configured to multiplex a plurality of amplified signals to reduce the number of conductors exiting the sensing assembly the external processing assembly is configured to convert a plurality of analog signals into digital signals to enable read-out of the data on a computer interface the neural probe and associated circuitry are part of an integrated device created using a complementary metal-oxide semiconductor (CMOS) fabrication process a data processing assembly configured to be located on a skull of the brain and to transmit digital data via a wireless or wired connection a power assembly configured to be located on a skull of the brain and to provide power to the sensing assembly located inside the brain the power assembly is configured to be charged via electrodynamic wireless power transmission, inductive power transmission, or resonant power coupling a deep brain stimulation system a neural probe configured for placement within a brain at least one signal lead extending from the neural probe a sensing assembly included on the neural probe the sensing assembly includes at least one sensing micro-electrode positioned on the neural probe and at least one stimulation electrode positioned on the neural probe at least one processor assembly receive, via the at least one signal lead, at least one sense signal generated in response to interaction between the at least one sensing electrode and one or more electrical signals generated by at least one neuron in the brain deliver at least one of a library of preset target stimulation patterns determine a target stimulation pattern based on at least one characteristic of the at least one sense signal cause a signal generator to deliver, via the at least one signal lead, one or more stimulation signals to a set of stimulation electrodes among the at least one stimulating electrode to activate the set of stimulation electrodes according to the target stimulation pattern the set of stimulation electrodes includes at least one of the plurality of dual-role micro-electrodes the set of stimulation electrodes includes two or more of the dual-role micro-electrodes the set of dual-role electrodes is spatially distributed relative to the neural probe the set of stimulation electrodes is selected based on the target stimulation location the at least one sensing electrode is configured to serve also as a stimulation electrode the at least one stimulating electrode is configured to serve also as sensing electrode a first stimulation signal delivered to a first stimulation electrode within the set of stimulation electrodes differs in at least one respect from a second stimulation signal delivered to a second stimulation electrode within the set of stimulation electrodes the at least one signal lead has a length of at least 40 mm the at least one signal lead has a length of at least 70 mm the at least one characteristic of the at least one sense signal comprises one or more of a frequency, waveform, amplitude, or integration of a waveform associated with the at least one sense signal the at least one characteristic of the at least one sense signal comprises an identification of a particular electrode from which the at least one sense signal originated the at least one characteristic of the at least one sense signal comprises a location of an electrode from which the at least one sense signal originated the at least one characteristic of the at least one sense signal comprises a variation in time of at least one of a frequency, waveform, amplitude, or integration of a waveform associated with the at least one sense signal the at least one sensing electrode is configured to sense electrical signals from neurons within a 200-micron radius from an area of the neural probe on which the at least one sensing electrode is located the at least one processor is further configured to determine the target stimulation pattern based on an observed change in the at least one characteristic of the at least one sense signal the at least one processor is further configured to cause the signal generator to deliver the one or more stimulation signals after receiving an input indicating user approval the at least one processor is configured to adjust one or more aspects of the target stimulation pattern based on received user input Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A deep brain stimulation system, comprising:
   a neural probe configured for placement within a brain;
   at least one signal lead extending from the neural probe;
   a sensing assembly included on the neural probe, where the sensing assembly includes at least one sensing micro-electrode positioned on the neural probe and a plurality of stimulation electrodes positioned on the neural probe, wherein the at least one sensing micro-electrode has a surface area of between 100 and 300 square microns; and
   at least one processor assembly configured to:
     receive, via the at least one signal lead, at least one sense signal generated in response to interaction between the at least one sensing micro-electrode and one or more electrical signals generated by a single neuron in a deep brain region of the brain, such that the at least one sensing micro-electrode provides single-neuron sensing resolution of action potentials in the deep brain region;
     determine a target stimulation pattern based on at least one characteristic of the at least one sense signal; and
     cause a signal generator to deliver, via the at least one signal lead, one or more stimulation signals to a set of stimulation electrodes among the plurality of stimulating electrodes to activate the set of stimulation electrodes according to the target stimulation pattern, wherein at least one of the set of stimulation electrodes is configured to stimulate the deep brain region with single-neuron resolution.

2. The deep brain stimulation system of claim 1, wherein the set of stimulation electrodes includes the at least one sensing micro-electrode.

3. The deep brain stimulation system of claim 1, wherein the at least one sensing assembly includes a plurality of sensing micro-electrodes, and the set of stimulation electrodes includes two or more of the plurality of sensing micro-electrodes.

4. The deep brain stimulation system of claim 1, wherein the at least one sensing assembly includes a plurality of sensing micro-electrodes, and the plurality of sensing micro-electrodes are spatially distributed relative to the neural probe and wherein the set of stimulation electrodes is selected based on the target stimulation location.

5. The deep brain stimulation system of claim 1, wherein the at least one sensing electrode is configured to serve also as a stimulation electrode.

6. The deep brain stimulation system of claim 1, wherein at least one stimulating electrode of the plurality of stimulating electrodes is configured to serve also as sensing electrode.

7. The deep brain stimulation system of claim 1, further configured to deliver a first stimulation signal to a first stimulation electrode within the set of stimulation electrodes and a second stimulation signal to a second stimulation electrode within the set of stimulation electrodes, wherein the first stimulation signal differs in at least one respect from the second stimulation signal.

8. The deep brain stimulation system of claim 1, wherein the at least one signal lead has a length of at least 40 mm.

9. The deep brain stimulation system of claim 1, wherein the at least one signal lead has a length of at least 70 mm.

10. The deep brain stimulation system of claim 1, wherein the at least one characteristic of the at least one sense signal comprises one or more of a frequency, waveform, amplitude, or integration of a waveform associated with the at least one sense signal.

11. The deep brain stimulation system of claim 1, wherein the at least one characteristic of the at least one sense signal comprises an identification of a particular electrode from which the at least one sense signal originated.

12. The deep brain stimulation system of claim 1, wherein the at least one sensing micro-electrode includes a plurality of sensing micro-electrodes, and wherein the at least one characteristic of the at least one sense signal comprises a location of an electrode, from among the plurality of sensing micro-electrodes, from which the at least one sense signal originated.

13. The deep brain stimulation system of claim 1, wherein the at least one characteristic of the at least one sense signal comprises a variation in time of at least one of a frequency, waveform, amplitude, or integration of a waveform associated with the at least one sense signal.

14. The deep brain stimulation system of claim 1, wherein the at least one sensing micro-electrode is configured to sense electrical signals from neurons within a 200-micron radius from an area of the neural probe on which the at least one sensing micro-electrode is located.

15. The deep brain stimulation system of claim 1, wherein the at least one processor is further configured to determine the target stimulation pattern based on an observed change in the at least one characteristic of the at least one sense signal.

16. The deep brain stimulation system of claim 1, wherein the at least one processor is further configured to cause the signal generator to deliver the one or more stimulation signals after receiving an input indicating user approval.

17. The deep brain stimulation system of claim 1, wherein the at least one processor is configured to adjust one or more aspects of the target stimulation pattern based on received user input.

18. The deep brain stimulation system of claim 1, wherein the at least one sensing micro-electrode has an impedance between 1 kOhms and 1 MOhm.

19. The deep brain stimulation system of claim 1, wherein the at least one of the set of stimulation electrodes has an impedance between 1 kOhms and 1 MOhm.

* * * * *